(12) United States Patent
Rainer et al.

(10) Patent No.: US 9,120,847 B2
(45) Date of Patent: *Sep. 1, 2015

(54) ISOLATION OF PHOSPHOPROTEINS, GLYCOPROTEINS AND FRAGMENTS THEREOF

(71) Applicants: Matthias Rainer, Grinzens (AT); Douglas T. Gjerde, Saratoga, CA (US); Guenther Bonn, Zirl (AT)

(72) Inventors: Matthias Rainer, Grinzens (AT); Douglas T. Gjerde, Saratoga, CA (US); Guenther Bonn, Zirl (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/744,305

(22) Filed: Jan. 17, 2013

(65) Prior Publication Data

US 2014/0200330 A1     Jul. 17, 2014
US 2014/0329991 A9     Nov. 6, 2014

Related U.S. Application Data

(63) Continuation-in-part of application No. 13/270,148, filed on Oct. 10, 2011.

(60) Provisional application No. 61/391,606, filed on Oct. 9, 2010, provisional application No. 61/498,510, filed on Jun. 17, 2011.

(51) Int. Cl.
    *C07K 1/30*          (2006.01)
    *C07K 1/32*          (2006.01)
    *C08L 33/00*       (2006.01)

(52) U.S. Cl.
CPC ..................................... *C07K 1/303* (2013.01)

(58) Field of Classification Search
CPC combination set(s) only.
See application file for complete search history.

(56) References Cited

PUBLICATIONS

Mario Pink et al (Precipitation by lanthanum ions: A straightforward approach to isolating phosphoproteins (Journal of Proteomics vol. 75, Issue 2, Dec. 21, 2011, pp. 375-383)).*
Guzel et al (Highly efficient precipitation of phosphoproteins using trivalent europium, terbium, and erbium ion Anal Bioanal Chem. May 2012;403(5):1323-31. Epub Mar. 27, 2012.*

* cited by examiner

*Primary Examiner* — Kagnew H Gebreyesus
(74) *Attorney, Agent, or Firm* — Sue S. Kalman

(57) ABSTRACT

The invention provides methods and apparatus for the selective isolation of phosphorylated and glycosylated proteins and their fragments. A lanthanide metal cation is used to precipitate proteins or protein fragments containing phospho groups and/or glyco groups. The sample preparation method can be used for many types of biological samples, including HeLa cells, food, and human cerebrospinal fluid. The proteins are isolated, recovered and ready for analysis by mass spectrometry or other analytical methods allowing detection limits down to the femtomole level. The method and apparatus are valuable tools in the field of protein analysis and diagnostics.

15 Claims, 7 Drawing Sheets

Labeled peaks: (1) $[M+2H]^{2+}$ α-casein, (2) $[M+H]^+$ lysozyme, (3) $[M+H]^+$ myoglobin and (4) $[M+H]^+$ α-casein.

Labeled peaks: (1) [M+2H]$^{2+}$ caseins, (2) [M+H]$^+$ α-lactalbumin, (3) [M+H]$^+$ β-lactoglobulin and (4) [M+H]$^+$ αS1-casein, (5) [M+H]$^+$ β-casein and (6) [M+H]$^+$ αS2-casein.

Labeled peaks: (1) lectin from fava beans (glycoprotein), (2) beta-casein (phosphoprotein).

Labeled peaks: (1) lectin from fava beans (glycoprotein), (2) beta-casein (phosphoprotein).

ISOLATION OF PHOSPHOPROTEINS, GLYCOPROTEINS AND FRAGMENTS THEREOF

CROSS REFERENCE TO RELATED APPLICATIONS

This application is a continuation in part of U.S. application Ser. No. 13/270,148, filed Oct. 10, 2011, which claims the benefit of U.S. Provisional Application No. 61/391,606, filed Oct. 9, 2010 and U.S. Provisional Application No. 61/498,510, filed Jun. 17, 2011, all of which are incorporated by reference herein.

BACKGROUND OF THE INVENTION

This invention relates to methods for the isolation of phosphoproteins and glycoproteins and fragments of proteins for the analysis of biological samples, including biological fluids, biological cultures, cell cultures, cell lysates, cell-free cultures, yeast, HeLa cells, food, blood, urine, tissue and human cerebrospinal fluid.

Protein phosphorylation is the enzymatic process performed by kinases of adding phosphate group(s) to a protein. Phosphorylation is a reversible post translational modification that is important in many different cellular pathway processes including those involving enzymatic activities. It is estimated that up to a third of the proteins contained in a cell can be phosphorylated at some point in the life cycle of any particular protein (Hubbard, M. J. et al. (1993) Trends Biochem. Sci. 5, 172-177). Phosphorylation of proteins that are contained in eukaryotic cells occurs mainly on serine, threonine, and tyrosine residues with serine being the most frequently modified amino acid. One study performed on HeLa cell phosphorylation site distribution reported the relative concentration of the phosphoserine, phosphothreonine, and phosphotyrosine sites at 86.4, 11.8, and 1.8%, respectively (Olsen, J. et al. (2006) Cell. 127, 635-648).

Substantial work has been devoted to the development and improvement of methods for selective enrichment of phosphopeptides (Trojer, L., et al. (2005) J. Chromatogr. A. 1079, 197-207; Feuerstein, I. et al. (2006) J. Am. Soc. Mass Spectrom. 17, 1203-1208; Valiant, R. M. et al. (2007) Anal. Chem. 79, 8144-8153; Feuerstein, I. et al. (2005) Proteomics. 5, 46-54) but not phosphoprotein enrichment. The isolation of low concentrations of a phosphorylated protein fragment from its non-phosphorylated counterpart and a mixture of polypeptides has been shown to be difficult. Even more difficult is separating a phosphorylated protein from a mixture containing its non-phosphorylated counterpart and other proteins. The reason for this is unknown but may be because the number of phosphorylated sites on a given protein is small.

Two common strategies are currently employed for the isolation of phosphopeptides: immobilized metal ion affinity chromatography (IMAC) and metal oxide affinity chromatography (MOAC). IMAC is the most widely used strategy for phosphopeptide enrichment. This technique was initially developed in 1975 and was originally used to separate His-tagged proteins (Porath, J. et al. (1975) Nature. 258, 598-599). IMAC resins containing iron and gallium are the commonly used metals for the enrichment of phosphorylated species (Bonn, G. K. et al. (1990) Chromatographia. 30, 9/10; Aprilita, N. H. et al. (2005). J. Proteome Res. 4, 2312-2319; Sykora, C. et al. (2007) Protein & Peptide Letters. 14, 489-496). The other chemical strategy, MOAC (Wolschin, F. et al. (2005) Proteomics. 5, 4389-4397) employs metal oxides such as titanium dioxide ($TiO_2$) (Mazanek, M. et al. (2007) Nat. Protoc. 2, 1059-1069), zirconium dioxide ($ZrO_2$) (Zhou, H. et al. (2007) Electrophoresis. 28, 2201-2215; Kweon, H. K. et al. (2006) Anal. Chem. 78, 1743-1749) or mixed $TiO_2/ZrO_2$ nanoparticles embedded in a monolithic polymer (Rainer, M. et al. (2008) Proteomics. 8, 4593-4602) to selectively retain phosphopeptides from complex biological samples. In several studies, aluminum hydroxide and aluminum oxide were shown to exhibit a high and selective attraction to phosphorylated proteins (Chang, M. F. et al. (1997) J. Pharm. Sci. Technol. 51, 25-29; Lyer, S. et al. (2003) Pharm. Dev. Technol. 8, 81-86). After capture and isolation of the phosphopeptides, analysis is often performed by mass spectrometry.

More recently, a two-step phosphopeptide enrichment method was reported in which calcium cations are used to help isolate the phosphopeptides and then IMAC was used for final purification of the precipitated peptides (Zhang, H. et al. (2007) Molec. and Cell. Prot. 6.11, 2032-2042). However, the researchers found that calcium cation did not precipitate the phosphopeptides contained in a mixture. When calcium cation was added to the mixture, no precipitate was formed. Instead, a phosphate ion solution was added to the trypsin digested sample first. Then, with the phosphate present in the digested sample, calcium cation was added to the digested sample solution to precipitate calcium phosphate. Using this procedure, the calcium phosphate precipitate also pulled down the phosphopeptides that became associated with the calcium phosphate precipitate. After this process, it was further discovered that IMAC was needed for additional purification and enrichment to remove non phosphopeptides that also became associated with the calcium phosphate precipitate. Phosphoproteins, glycoproteins and glycopeptides could not be recovered by these researchers.

Glycoproteins play an essential role in the body. For instance, in the immune system, almost all of the key molecules involved in the immune response are glycoproteins. The analysis or determination of protein glycosylation has become an important goal for biomarker studies since it has long been known that cellular glycosylation profiles change significantly during oncogenesis, the process whereby normal cells are transformed to cancer cells (Hakomori, S. (1996) Cancer Res. 56, 5309-5318; Kobata, A. (1998) Glycoconj J. 15, 323-331). Similar to phosphoprotein and protein fragment isolation and analysis, the isolation and analysis of the glycoproteome presents a significant challenge for the bioanalytical chemist. The most common approach for the enrichment of glycosylated proteins is based on isolation by lectin affinity resins (Zhao, J. et al. (2006) J. Proteome Res. 5 (7), 1792-1802). A number of different resin types have been used to capture various types of glycoproteins. After enrichment and elution, the species are digested and then usually deglycosylated by protein-N-glycanase F. Finally, the proteins and the glycosylation sites are identified, primarily by mass spectrometry (Xiong, L. et al. (2003) J. Proteome Res. 2, 618-625; Alvarez-Manilla, G. et al. (2006) J. Proteome Res. 5, 701-708; Zhang, L. et al. (2005) Anal. Chem. 77, 7225-7231; Wang, Y. et al (2006) Glycobiology. 16, 514-523).

Phosphoproteins and glycoproteins and their peptides are important for general biological research and are potentially important biomarkers that could be used for the diagnosis of disease. The ability to capture both species together or separately is desirable. There exists a need to be able to distinguish between phosphoproteins and glycoproteins. There exists a need to capture, at will, both phosphoproteins and glycoproteins together or separately and selectively.

Valuable biological information can be obtained by capturing whole phosphorylated and glycosylated proteins rather than merely capturing their fragments. When enzymatic digestion is performed on a protein mixture, the resulting mix of polypeptides is very complex, composed of fragments originating from many different proteins. Analysis of this mixture requires attempting to determine the starting protein from which each particular polypeptide originated. Capturing whole phosphoproteins (or glycoproteins) and performing top down analysis simplifies the sample and provides additional insight into the position or positions that are phosphorylated (or glycosylated) on any particular protein. Once whole functionalized proteins are captured, chromatography or gel electrophoresis can be used to separate and collect individual proteins prior to enzymatic digestion.

Therefore, there exists a need for the ability to isolate phosphoproteins and/or glycoproteins in a reproducible manner, especially when they are present at very low concentrations.

SUMMARY OF THE INVENTION

The invention provides methods for the selective isolation of phosphorylated and glycosylated proteins and their fragments. Selective metal cations are used to precipitate phosphoproteins and/or glycoproteins from complex mixtures. Selective metal cations may be used to precipitate polypeptides containing phospho and/or glycan groups from complex mixtures. Lanthanide metals work particularly well for this purpose. For example, lanthanum (III) is used to preferentially complex into a precipitate the phosphate group and the glyco group, particularly N-linked glyco groups, contained on proteins or fragments of proteins allowing their isolation from complex mixtures. The invention also allows the controlled release and isolation of protein and protein fragments containing glycans from the initial precipitate leaving the phosphoproteins. Proteins containing phospho or glyco groups can be digested (and analyzed) while they are contained in the precipitation pellet or after the pellet containing the proteins has been dissolved. Proteins containing glyco groups can be digested and analyzed after the proteins containing these groups have been eluted from the pellet.

The precipitated proteins may be digested with an enzyme directly on the pellets formed from the method or any of the precipitates may be dissolved and treated with an enzyme. The sample preparation method and device can be used for many different types of biological samples, including biological fluids, biological cultures, cell cultures, cell lysates, cell-free cultures, yeast, HeLa cells, fresh milk, blood, urine, tissue and human cerebrospinal fluid. The proteins are precipitated, recovered and ready for analysis by methods such as electrophoresis, chromatography, mass spectrometry, IR or UV spectrometry, ELIZA, protein array, SPR or other analytical methods. The sample can be ready for analysis in as little as ten minutes and may allow detection limits down to the femtomole level and lower. The method and device are valuable tools in the field of protein analysis and diagnostics.

The application of lanthanide metals for the precipitation of phosphorylated and/or glycosylated proteins opens a new field of fast selective and sensitive biomarker analysis. The method can be used to determine biological pathways and mechanisms. The method was demonstrated for complex biological samples by being able to identify proteins present in the samples in low concentrations.

DETAILED DESCRIPTION OF THE INVENTION

Before describing the present invention in detail, it is to be understood that this invention is not limited to specific embodiments described herein. It is also to be understood that the terminology used herein for the purpose of describing particular embodiments is not intended to be limiting. As used in this specification and the appended claims, the singular forms "a", "an" and "the" include plural referents unless the context clearly dictates otherwise. Thus, for example, reference to polymer bearing a protected carbonyl would include a polymer bearing two or more protected carbonyls, and the like. Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, specific examples of appropriate materials and methods are described herein.

The invention provides methods and devices for the rapid and controllable precipitation of phosphoproteins, glycoproteins and their fragments. Phosphoproteins are proteins to which phosphate groups are covalently bound. A common example of a phosphoprotein is the protein casein found in milk. A glycoprotein is a molecule composed of a protein that contains oligosaccharide chains (glycans) covalently attached to polypeptide side-chains. A glycopeptide is similar in structure to a glycoprotein but consists of a chain of amino acids.

In the present invention, lanthanide metal cations are used to precipitate and complex the proteins in a sample containing either phosphate groups or glycans. These proteins can be analyzed together, or through further chemical manipulation, the pellet proteins containing the phosphate groups and/or the glyco groups can be isolated and analyzed. In some embodiments, lanthanide metals including Lanthanum (III) cations are utilized.

The characteristics of the method and device of this invention can be illustrated and performed in simple samples containing a protein mixture or in complex samples such as a biological matrix of cerebrospinal fluid. The sample preparation method and device can be used for any type of biological sample, including but not limited to biological fluids, biological cultures, cell cultures, cell lysates, cell-free cultures, yeast, HeLa cells, fresh milk, blood, urine, tissue and human cerebrospinal fluid. The recovered proteins can be analyzed by mass spectrometry or other analytical methods with detection limits at the femtomole level and lower. The method and devices are valuable tools in the field of protein analysis, biological research and diagnostics.

Figure 6:
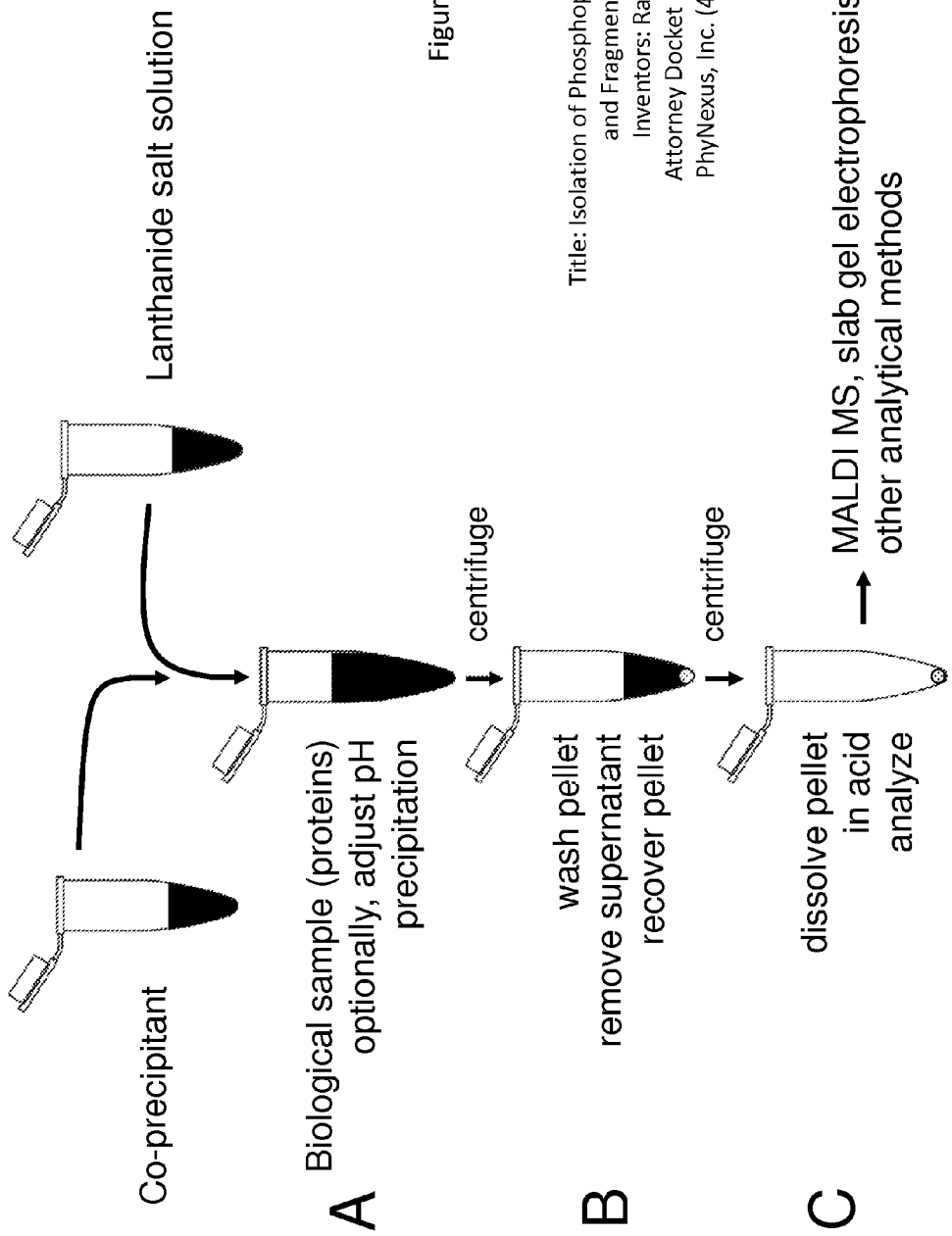
FIG. 6: Depicts embodiments of the workflow utilized for the isolation of phosphoproteins, phosphopeptides, glycoproteins and glycopeptides.

One embodiment of the isolation procedure of the invention is shown in FIG. 6. It should be noted that this procedure can be used to isolate phosphopeptides and glycopeptides as well as phosphoproteins and glycoproteins. The lanthanide metal is added to the sample to precipitate proteins. A number of different lanthanide salt solutions can be used in step A of FIG. 6. In one embodiment of the invention, an $ErCl_3$ solution is added to a biological sample. In other embodiments, any lanthanide salt can be used including $LaCl_3$, $HoCl_3$, $CeCl_3$, $TmCl_3$, $TbCl_3$ or combinations of these. In other embodiments, any soluble anion (e.g., nitrate) can be substituted for chloride.

In certain embodiments, the pH can be adjusted to 3 or less in step A. Co-precipitation of non-phosphorylated proteins is reduced under acidic conditions. In some embodiments the pH is adjusted by the addition of TFA. By acidifying the sample before centrifugation, many of the acidic residues (e.g., aspartate and glutamate side chains) become neutralized, while phosphate groups retain their negative charge and their binding affinity toward lanthanide ions. In some embodiments, the pH is adjusted to be below 1.9. However, low pH would not be expected to inhibit binding of glycoproteins. Instead, stringent wash steps with phosphate buffer can elute glycoproteins by replacing them.

The sample may be centrifuged at this point to recover the precipitate containing the phosphoproteins and/or glycoproteins. It should be understood that the precipitate can be recovered by any method used to separate liquids from solids.

Co-precipitant reagents such as phosphate may be added to increase the total precipitate mass. The addition of co-precipitants can be performed before centrifugation (FIG. 6, step A). In some embodiments, a co-precipitant such as $KH_2PO_4$ (or another form of phosphate) may be added to the solution. The addition of this co-precipitant does not have an effect on the initial metal protein precipitates formed. However, additional metal phosphate precipitate may be formed. In some embodiments the co-precipitant may be added before the metal ion in step A of FIG. 6. The increase in precipitate mass is caused by the excess unused (uncomplexed or unprecipitated) metal that may be present. In some embodiments, other co-precipitant anions may be added to the mixture to enhance the precipitate being formed. Non-limiting examples of co-precipitant anions are phosphate, carbonate, hydroxide and iodate.

It is remarkable that a metal can selectively bind with phophosproteins and/or glycoproteins to form a precipitate. It is not known how the precipitate forms, but presumably the precipitate structure would contain many protein molecules associated with each other in such a way that the proteins are insoluble. It is unknown how the proteins form the precipitate with the addition of the lanthanide metal ion.

Previous workers discovered that no precipitate is formed when calcium is added to a biological sample containing phosphopeptides (Zhang, H., et al. (2007) Molec. and Cell. Prot. 6.11, 2032-2042). Polypeptides are much smaller than proteins. However surprisingly and unexpectedly in this invention, lanthanide metals can be used to form a precipitate with phosphoproteins and glycoproteins when the metal is added to a biological sample. Proteins are very large molecules and the portion of the protein molecule containing the phospho groups or glyco groups can be a relatively small portion of the molecule. The selective precipitation of either phosphoproteins or glycoproteins from a sample is unexpected. Trivalent and higher-valent lanthanide metals such as erbium, terbium and europium are particularly effective. Lanthanum works well because it is inexpensive, forms a precipitate with both phosphoproteins and glycoproteins. In addition, it forms a protein precipitate at low concentrations of the metal ion and is relatively non-toxic.

Some lanthanide metals including europium, terbium and erbium are less effective or will not form glycoprotein precipitates. However, europium, terbium and erbium metals work well for the precipitation and recovery of phosphoproteins.

The precipitation method of the invention may be performed with centrifuges or by another method. The metal precipitating and complexing ion may be added as a liquid or be contained on an ion exchanger or other solid.

Additional precipitations enhancers can be added to the solution to enhance formation of the precipitate. These precipitation enhancers can be added prior to centrifugation (FIG. 6, step A). These additives include salts, organic solvents and water soluble polymers. A non-limiting list of water miscible organic solvents that could be added includes alcohols, ketones, aldehydes and other organics or mixtures thereof. Water soluble polymers including polyelectrolytes and non ionic polymers or mixtures may be added. Salts may be added to reduce the solubility of the precipitate. Salts may be added to form additional precipitates with any free or left over lanthanide ions that have not precipitated with the proteins.

The temperature of the solution can be varied. For example, the kinetic rate of precipitation can be increased by increasing the solution temperature. The amount of precipitate formed can be increased by decreasing the solution temperature.

Lanthanide metals will form phosphoprotein and/or glycoprotein precipitation complexes. Erbium works particularly well for isolation of phosphoproteins and phosphopeptides. Lanthanum metal is useful because it is nontoxic, inexpensive and effective. The solubility of the lanthanum phosphoproteins and glycoproteins precipitate complexes was found to be low. Rare earth metal salts of terbium, europium and erbium are very effective in forming precipitates with phosphoproteins.

In one embodiment, the biological sample is not denatured. However, denaturing the sample prior to addition of the metal may be used to improve the capture, digestion and analysis. In certain embodiments, the biological sample may be denatured to enhance or improve the ability of the lanthanide metals to precipitate the proteins. The term, "denatured biological sample", as used herein can include biological samples in which the proteins are partially denatured or samples in which a portion of the proteins are denatured.

Any method for denaturing the proteins within a biological sample can be used. A person having skill in the art can select an appropriate denaturing method. For example, the sample can be treated with heat, acid, base, alcohol, reducing agents A common denaturing agent is a mixture of dithiotreitol (DTT), 1-O-n-oxtyl-β-D-glucopyranoside (nOGP) and iodoacetamide (IAA). Although not wishing to be bound by theory, it is believed that this mixture helps denature the sample by breaking up the disulfide bonds by DTT and alkylating the thio groups with IAA. The nOGP is a nonionic detergent used with proteins. Due to air oxidation, DTT is a relatively unstable compound and should be stored by refrigeration and handling in an inert atmosphere. DTT becomes less potent as the pH lowers. (2S)-2-amino-1,4-dimercaptobutane (dithiobutylamine or DTBA) is a dithiol reducing agent that somewhat overcomes this limitation of DTT. Tris (2-carboxyethyl)phosphine HCl (TCEP hydrochloride) is an alternative reducing agent that is more stable and works even at low pH.

Denaturing the proteins can be performed at different stages in the process. When denaturing is performed prior to capture, the protein is denatured to help capture and precipitate the entire protein. In other examples, the protein may be denatured at a later stage for example, to improve digestion with an enzyme.

To demonstrate the value of denaturing the sample before precipitation, the following experiment was carried out. Two identical (1 mL) urine samples were analyzed. The first urine sample was prepared without denaturing. Lanthanum metal ion was added to the sample and a precipitate was formed and recovered. The second urine sample was denatured by the addition of 20 µL DTT (45 mM) and 20 µL of nOGP (40 mM) followed by vortex mixing at 95° C. for 5 min. After cooling down the sample to room temperature, 20 µL of IAA (100 mM) were added for the alkylation of the thiol groups. Afterwards, the sample was stored in the dark for 30 min. Lanthanum metal was added to the denatured sample and the precipitate was recovered into a pellet. The two pellets were digested with an enzyme and the supernatant digestion fraction was recovered for both samples. The digested fraction was analyzed by nanoLC-ESI-MS. The analysis conditions were as follows: PepMap LC Packings column, 50 cm×75 µm with a particle size of 3 µm and 120 Å pore size. The flow rate was 300 nL/min and the gradient from 100% A to 60% A in 120 min (A: $H_2O$, 3% ACN, 0.1% formic acid; B: 80% ACN, 20% $H_2O$, 0.1% formic acid).

The number of identified proteins after the two runs was compared. Without denaturing the sample, 101 proteins were identified (72 phosphorylated and 29 glycosylated). In the experiment performed by first denaturing the sample, 426 proteins were identified (288 phosphorylated and 138 glycosylated) showing the positive influence of the denaturing step. A denaturing step prior to precipitation is useful for enhanced recovery of both phosphoproteins and glycoproteins.

Lanthanide metal cations added to the sample solution will precipitate proteins and/or fragments thereof that contain phospho groups and/or glyco functional groups. The mechanism for the precipitation of phosphate-containing proteins with a lanthanide is unknown. For a precipitate to form, many molecules must be linked together to form a very large lanthanum phosphate-containing insoluble molecular structure. It is unexpected and surprising that a metal cation phosphoprotein precipitate can be formed and recovered since it was reported earlier that calcium does not form a precipitate with phosphopeptides, which are much smaller molecules (Zhang, H., et al. (2007) Molec. and Cell. Prot. 6.11, 2032-2042).

The forces and structure of a precipitate of lanthanum and a glycoprotein are even less understood and it is unexpected and surprising that a metal cation glycoprotein precipitate can be formed and recovered. It is possible that one or more lanthanum cations may form a structure with exposed hydroxide groups on the glycoprotein, but it is unknown how these lanthanide protein structures are configured and why they are strong enough and structured in way to be removed by precipitation. Lanthanum (III) has a preference for N-linked glycoproteins over other glycoproteins. Other metals will complex O-linked, C-linked, phospho linked and other glycoproteins.

The precipitate may remain in suspension in the sample or may fall out of solution. In one embodiment, the precipitate formed from the addition of metal ion such as lanthanum (III) to the biological sample may be centrifuged and processed to recover and analyze the phosphoproteins and glycoproteins or protein fragments in the sample. In another embodiment, the precipitated sample may be treated to selectively remove glycoproteins and recover only the phosphoproteins or phosphoprotein fragments. This is accomplished by addition of an anion such as $KH_2PO_4$ after precipitation of the sample. Addition of an anion at this stage is different from the co-precipitant described previously. In a previous embodiment, it was described that the addition of a co-precipitant (e.g., a phosphate anion) after the initial addition of the lanthanide cation will form a precipitate with the excess remaining lanthanide cation (uncomplexed lanthanide cation). It was discovered that the addition of the co-precipitant is beneficial because more precipitate mass is formed and it takes less centrifugation time to form the pellet. This procedure of the second addition of phosphate ion is different because no additional precipitate is formed.

To selectively isolate phosphoproteins, an anion is added after centrifugation. It was discovered unexpectedly and surprisingly, that if an anion (such as a phosphate) is added after centrifugation at sufficient concentration and without the excess metal present, it will "break up" or "displace" the lanthanide glycoprotein or glycoprotein fragments from the precipitate complex and the glycoproteins will be found in supernatant. At this stage, the supernatant containing glycoproteins (and their fragments) can be discarded while the phosphoproteins remain in the pellet. Other glycoprotein solubilizing reagents may be used to remove the glycoproteins. Non-limiting examples of such solubilizing reagents include boric acid, borate anion, barium, calcium, carbonate, hydroxide, lanthanum, oxalate or other anions.

In these embodiments, after the addition of phosphate anion, the glycoproteins will re-dissolve and remain in the supernatant along with the other non phosphoproteins and other biological material in the initial centrifugation. The pellet can be centrifuged, washed and the supernatant discarded. In this embodiment, the glycoproteins will be in the supernatant. Thus, the process carried out on the precipitated pellet from this point will result in the recovery and analysis of only phosphoproteins and protein fragments and not glycoproteins or glycoprotein fragments. However in other embodiments, the dissolved portion of the sample, the supernatant, can be taken to recover and analyze glycoproteins and glycopeptides.

The precipitate of lanthanide phosphoproteins and lanthanide glycoproteins formed in the initial precipitation reaction may be centrifuged. After the lanthanide protein precipitate is formed, the solution containing the precipitate and unused lanthanide ion may be treated with a phosphate buffer such as $KH_2PO_4$ solution to increase amount of precipitate obtained. In those embodiments in which a phosphate (or another anion) is added at this point or later, the phosphate ion may dissolve or breakup the glycoprotein complex and allow recovery the glycoproteins in the supernatant, leaving the phosphoproteins intact in the precipitate. At this point, either class of proteins could be processed and analyzed directly as whole proteins, with CE, HPLC, or MALDI for example, or digested with an enzyme and analyzed as polypeptides with HPLC and/or mass spectrometry.

After the pellet is formed, it is washed to remove materials not of interest (FIG. 6B). Water or different buffers or solutions can be used for the wash. In some embodiments, a lanthanide such as $LaCl_3$ can be used as a wash reagent. In these embodiments, the lanthanide is usually more dilute than the lanthanide salt solution added to the biological sample in FIG. 6, step A. In some embodiments, a buffer containing $KH_2PO_4$ can be used to inhibit the binding of acidic peptides and proteins to lanthanum and to wash these materials from the pellet. Several amino acids are acidic and may lower the pI of a polypeptide or proteins. Body fluid samples may contain many polypeptides. Polypeptides may be formed by enzymatic digestion. Peptides with Asn or Asp amino acid residues may bind $La^{3+}$ and coprecipitate and may need to be washed from the pellet. In some embodiments, after the pellet is formed, the precipitate can be treated with a denaturing solvent such as urea and a denaturing surfactant such as CHAPS. In some embodiments, a low pH wash solvent (such as an acid) is used. In certain embodiments, the wash contains carbonate, oxalate or hydroxide.

In some embodiments, the wash solution can select for the glycoproteins. An example of this is boric acid or sodium borate solution. Alternatively, the wash solution could displace the glycoproteins. Examples of this are carbonate, oxalate, or hydroxide containing solutions. A solution of a $KH_2PO_4$ solution (e.g. 4 M) can be used to extract or elute the proteins from the metal precipitate pellet.

The phosphoproteins or phosphopeptides that are bound to the precipitate remain bound (as part of the precipitate) but will denature. Denaturation will help remove nonspecifically-bound proteins associated with the protein interaction by non-covalent interactions. It should be noted that the description "proteins remain bound" is used here to describe proteins within the pellet or precipitate, but the mechanism and form by which the functionalized proteins are associated with the precipitate is unknown. The denaturing treatment may be performed with the precipitate in suspension. The pellet with bound, denatured phosphoproteins and/or glycoproteins or protein fragments can be reformed by centrifugation and then the pellet can be washed by repeated re-suspension and centrifugation in deionized water or buffer. In one embodiment, one denaturing step is used and four washing steps are used but any number of denaturing and washing steps may be used.

After the final wash step, the bound functionalized proteins can be recovered by re-suspending and then dissolving the pellet into solution by lowering the solvent pH (FIG. 6C). Acids such as formic acid, phosphoric acid, hydrochloric acid, TFA and others can be used for this step.

After dissolving the pellet, the solution containing the functionalized protein or protein fragments may be analyzed by mass spectrometry, gel electrophoresis, 2D-gel electrophoresis or any analytical method including chromatography, capillary electrophoresis, etc.

In one embodiment, the digestion of the proteins with an enzyme may be performed after re-dissolving the pellet. In another embodiment, the whole proteins or protein fragment bound to the precipitate may be digested on pellet with an enzyme. Then peptides released by the digestion may be analyzed by LC-MS or other techniques to determine the peptide mass fingerprint and location of the functional groups.

DEFINITIONS

The terms, "lanthanides", "lanthanide metals" and "lanthanoids" are used herein as equivalents and refer to the chemical elements with atomic numbers 57 through 71.

The terms "protein fragment", "fragments of protein", "peptides" and "polypeptides" are equivalent terms in describing a part or portion of a protein.

The terms "bound", "precipitate", "complex", "precipitate complex" and "solid phase" are equivalent terms in describing the precipitate.

The terms "glycoproteins" and "glycosylated proteins" are considered equivalent terms herein.

The terms "phosphoproteins" and "phosphorylated proteins" are considered equivalent terms used in the method of the invention.

The terms phosphoprotein or protein having a phospho functional group are considered equivalent terms used in the method of the invention. The terms glycoprotein, glycan or protein having a glyco functional group are considered equivalent terms used in the method of the invention.

The terms functionalized protein (or polypeptide) as used herein refers to proteins or polypeptides comprised of phospho or glyco groups.

The following abbreviations are used herein. (nOGP) n-Octyl-β-D-glucopyranosid, (IAA) iodoacetamide, (CSF) cerebrospinal fluid, (AD) Alzheimer's disease, (FA) formic acid, (SA) sinapinic acid, (DHB) 2,5-dihydroxybenzoic acid, (PMF) peptide finger print, (PTM) posttranslational modification, (DTT) dithiothreitol, (TFA) trifluoroacetic acid, (TCEP) Tris(2-carboxyethyl) phosphine and (ApoE) apolipoprotein E.

Table 1 is an example of the steps of the method along with function, different options and comments. It is only for illustrative purposes and not meant to limit the invention. Although lanthanum (III) is the exemplified metal cation for preparing precipitates with phosphoproteins and glycoproteins and proteins fragments, other lanthanide metals may also be used in this procedure and the procedures described in the text and other tables.

Having now generally described the invention, the same will be more readily understood through reference to the following examples, which are provided by way of illustration, and are not intended to be limiting of the present invention, unless so specified.

EXAMPLES

The following preparations and examples are given to enable those skilled in the art to more clearly understand and practice the present invention. They should not be construed as limiting the scope of the invention, but merely as being illustrative and representative thereof.

Example 1

The Precipitation of Phosphoproteins

In this example, the washing steps remove nonspecifically-bound proteins, particularly glycosylated proteins. Precipitation can be performed using different lanthanide metal ions.

TABLE 1

Method for the isolation of phosphorylated proteins by Lanthanide (e.g., La, Ce, Eu, Er, Tb, Ho, Tm) precipitation. It should be noted that other metals may be substituted for this method. Comments and some of the possible variations on the method are included in the table.

| Step | Description | Amount, volume, etc. | Function | Comment |
|---|---|---|---|---|
| 1 | Provide phosphorylated protein sample | Typically 10-1000 µL of sample | | Can be from cancer cells or human cerebrospinal fluid, etc. The sample may be whole protein or be digested to provide polypeptides or fragments of proteins. The sample may be denatured. |

TABLE 1-continued

Method for the isolation of phosphorylated proteins by
Lanthanide (e.g., La, Ce, Eu, Er, Tb, Ho, Tm) precipitation.
It should be noted that other metals may be substituted for this method. Comments
and some of the possible variations on the method are included in the table.

| Step | Description | Amount, volume, etc. | Function | Comment |
|---|---|---|---|---|
| 2 | Add lanthanide chloride Solution (La, Ce, Eu, Er, Tb, Ho, Tm), mix sample by vortex | 1.5-7 µL of 2M $ErCl_3$ larger volumes are used for larger sample volumes. | Forms insoluble salt complex with phosphorylated proteins. The phosphate anion forms $Er(PO_4)$ ppt with left over or unused metal cation (any Er that did not bind to a protein). | Smaller and larger sample sizes are possible with proper adjustment of reagents. In some embodiments the sample pH may be adjusted before step 2 in order to reduce interaction of the metal ion with acetic groups on the proteins. Cloudy solution is formed with some particulate falling to the bottom of vial. Other lanthanide metals will also form salt and complex insoluble precipitates. The erbium protein precipitate can be centrifuged at this point. |
| 3 | Add $KH_2PO_4$, mix sample by vortex | 1-10 µL of 2M $KH_2PO_4$, larger volumes are used for larger sample volumes | Supports precipitation of phosphoproteins in the presence of $ErCl_3$ and allows easier handling of the pellet. | In some embodiments the addition of phosphate ion can be performed before step 2. |
| 4 | Spin down to form pellet | | | |
| 5 | Re-suspend and wash the pellet once with 80 mM $ErCl_3$ and then spin down again | 80 mM $ErCl_3$ or $CaCl_3$ or others | Removes non-specific adsorbed components. | Also, removes any non-specific adsorbed protein. This step might be repeated for one or two more times. Other wash solvents may also be used. |
| 6 | Re-suspend and wash the pellet 1 to 2 times with dihydroxy-benzoic acid (DHB) solution | (110 mM DHB in 0.5% ACN/0.5% TFA | Removes non-specific adsorbed components. | Acts as displacer for acidic proteins and peptides. |
| 7 | Re-suspend and wash the pellet 1 to 2 times with DI water spinning down after each wash | De-ionized water (100 to 500 µL) | Removes excessive salts and metal ions. | |
| 8 | Re-dissolve pellet | 30 µL of formic acid or 0.2% of hydrochloric acid | Releases the proteins | Top down sample prep |
| 9 | CE, MALDI or other method analysis | | | Top down analysis |

For the precipitation of phosphorylated peptides the protocol in Table 2 can be used. In particular, the addition of $KH_2PO_4$ is performed before the addition of lanthanide metal ions.

TABLE 2

Method for the isolation of phosphorylated peptides by
Lanthanide (e.g., La, Ce, Eu, Er, Tb, Ho, Tm) precipitation.
It should be noted that other metals may be substituted for this method. Comments
and some of the possible variations on the method are included in the table.

| Step | Description | Amount, volume, etc. | Function | Comment |
|---|---|---|---|---|
| 1 | Provide phosphorylated | Typically 10-1000 µL of | | Can be from cancer cells or human cerebrospinal |

TABLE 2-continued

Method for the isolation of phosphorylated peptides by
Lanthanide (e.g., La, Ce, Eu, Er, Tb, Ho, Tm) precipitation.
It should be noted that other metals may be substituted for this method. Comments
and some of the possible variations on the method are included in the table.

| Step | Description | Amount, volume, etc. | Function | Comment |
|---|---|---|---|---|
|  | peptide sample | sample |  | fluid, etc. The sample may be digested to provide polypeptides or fragments of proteins. Smaller and larger sample sizes are possible with proper adjustment of reagents. In some embodiments the sample pH may be adjusted before step 2 in order to reduce interaction of the metal ion with acetic groups on the peptides. |
| 2 | Add $KH_2PO_4$, mix sample by vortex | 1-10 µL of 2M $KH_2PO_4$, larger volumes are used for larger sample volumes | Supports precipitation of phosphopeptides in the presence of $LaCl_3$ and allows easier handling of the pellet. | In some embodiments the addition of phosphate ion can be performed after step 3. |
| 3 | Add lanthanide chloride Solution (La, Ce, Eu, Er, Tb, Ho, Tm), mix sample by vortex | 1.5-7 µL of 2M $LaCl_3$, larger volumes are used for larger sample volumes. | Forms insoluble salt complex with phosphorylated peptides. The phosphate anion forms $La(PO_4)$ ppt with left over or unused metal cation (any La that did not bind to a peptide). | Cloudy solution is formed with some particulate falling to the bottom of vial. Other lanthanide metals will also form salt and complex insoluble precipitates. Lanthanum peptide precipitate can be centrifuged at this point. |
| 4 | Spin down to form pellet |  |  |  |
| 5 | Re-suspend and wash the pellet once with 80 mM $LaCl_3$ and then spin down again | 80 mM $LaCl_3$ or $CaCl_3$ | Removes non-specific adsorbed components. | Also, removes any non-specific adsorbed peptides. This step might be repeated for one or two more times. Other wash solvents may also be used. |
| 6 | Re-suspend and wash the pellet 1 to 2 times with dihydroxy-benzoic acid (DHB) solution | 20 mg/mL DHB in 2% ACN/0.1% TFA | Removes non-specific adsorbed components. | Acts as displacer for acidic peptides. |
| 7 | Re-suspend and wash the pellet 1 to 2 times with hydrochloric acid | 10 to 500 µL 0.2% hydrochloric acid | Removes non-specific adsorbed components. | Other buffers or acids may be used. |
| 8 | Re-dissolve pellet | 10 to 100 µL 2% of hydrochloric acid | Releases the peptides | bottom up sample prep |
| 9 | CE, MALDI-MS, LC-MS or other method analysis |  |  | bottom up sample prep |

Example 2

Method for the Isolation of Phosphorylated and Glycosylated Proteins by Lanthanum (III) Precipitation

TABLE 3

Method for the isolation of phosphorylated and glycosylated proteins by Lanthanum (III) precipitation. Other lanthanide metals may be substituted for this method. Comments and some of the possible variations on the method are included in the table.

| Step | Description | Amount, volume, etc. | Function | Comment |
| --- | --- | --- | --- | --- |
| 1 | Provide phosphorylated protein and/or glycoprotein sample | Typically 10-1000 µL of sample | | Can be from cancer cells or human cerebrospinal fluid, etc. The sample may be whole protein or be digested to provide polypeptides or fragments of proteins. The sample may be denatured. Smaller and larger sample sizes are possible with proper adjustment of reagents. In some embodiments the sample pH may be adjusted before step 2 in order to reduce interaction of the metal ion with acetic groups on the proteins. |
| 2 | Add Lanthanum (III), mix sample by vortex | 1.5-7 µL of 1M $LaCl_3$, larger volumes are used for larger sample volumes. | Forms insoluble salt complex with phosphorylated proteins. Forms insoluble complex with glycosylated proteins. | Cloudy solution is formed with some particulate falling to the bottom of vial. Other lanthanide metals will also form salt and complex insoluble precipitates. Lanthanum protein precipitate can be centrifuged at this point. |
| Optional 3 | Add $KH_2PO_4$, mix sample by vortex | 1-5 µL of 2M $KH_2PO_4$, larger volumes are used for larger sample volumes | The phosphate anion forms $La(PO_4)$ ppt with left over or unused metal cation (any La that did not bind to a protein). | In some embodiments the addition of phosphate ion can be performed before step 2. The precipitates of La-protein and $La(PO_4)$ can be centrifuged at this point. |
| 4 | Centrifuge to form pellet | | | |
| Optional 5 | Re-suspend and wash the pellet once with urea and CHAPS in PBS buffer and then centrifuge again | 500 µL of 8M urea/1% CHAPS in PBS pH 7.4 | Denatures precipitated protein in pellet | Also, removes any non-specific adsorbed protein. Surfactant may also be added earlier with the addition of Lanthanum. |
| 6 | Re-suspend and wash the pellet 3 times with DI water, centrifuging after each wash | De-ionized water | Removes excess urea and surfactant and non-specific adsorbed protein | Different buffers may be used to wash away materials not of interest. |
| Optional 7 | Treat pellet with phosphate ion | 10-300 µL of 4M $KH_2PO_4$ and de-ionized water | Breaks up and dissolves any La-glycoprotein precipitate. Phosphoproteins remain in the pellet. Glycoproteins are in the supernatant and are optionally recovered and analyzed by top down or bottom analysis. | The pellet may be treated with phosphate prior to or following separation by centrifugation or another method. No extra co-ppt was formed because excess La (III) has been removed. The amount of phosphate anion added can be adjusted to remove all of the glycoproteins. Gel electrophoresis and other techniques can be used to measure the effectiveness of the reagent. |
| Optional 8 | Re-suspend and wash the pellet 3 times with DI water, centrifuging after each wash | De-ionized water (500 µL) | | |

TABLE 3-continued

Method for the isolation of phosphorylated and glycosylated proteins by Lanthanum (III) precipitation. Other lanthanide metals may be substituted for this method. Comments and some of the possible variations on the method are included in the table.

| Step | Description | Amount, volume, etc. | Function | Comment |
|---|---|---|---|---|
| Optional 9 | On pellet microwave-assisted trypsin digestion | Several steps | Releases fragments of proteins through digestion | Bottom up sample prep. . |
| Optional 10 (follows optional 9) | uLC-ESI-MS analysis or other method on supernatant | | | Bottom up analysis. Proteins can be identified by MS/MS. |
| Optional 11 | Re-dissolve pellet | 10 µL of 2.5% $H_3PO_4$ | Releases the proteins | Top down sample prep |
| Optional 12 (follows optional 11) | CE, MALDI or other method analysis | | | Top down analysis |

In this example, only a slight (20%) molar excess of a lanthanum (III) compound is needed to achieve complete precipitation although in practice the lanthanide metal is used in greater molar excess ensuring complete capture of unknown concentrations of proteins. Sample precipitation pellets in step 2 may be formed from a progression of metal concentrations. The pellets can be analyzed by gel electrophoresis (or other protein analysis methods) to determine whether a sufficient and optimum amount of metal has been used to capture proteins. The lanthanide metal amount can be increased until no new proteins are captured.

The precipitation process of proteins is unknown. A protein is large and bulky but presumably the functional group on the protein such as a phosphate group or a glyco group would take up only a very small portion of the protein molecule. The nature of the lanthanide metal protein precipitate is unknown, but in order for a particular protein type to precipitate it must form a large, presumably multiprotein metal complex perhaps linking multiple protein molecules and multiple metal molecules. The mechanism by which a multiprotein linked complex could be formed is unknown.

The sample pellets and supernatants obtained from a progression of phosphate concentrations (Table 3, optional step 7) can be analyzed by gel electrophoresis (or other protein analysis methods) to determine whether a sufficient or optimum amount of phosphate has been used to remove and capture glycoproteins. The phosphate amount can be increased until no additional protein is removed from the pellet or no new protein is recovered in the supernatant.

Example 3

Method for the Isolation of Phosphorylated and Glycosylated Proteins by Lanthanum (III) Precipitation The procedure outlined in Table 4 is similar to the procedure in Table 3 except that in this example the amounts of reagent are shown for a 50 µL sample. Also in this example, the sample is denatured prior to precipitation to facilitate (selective) precipitation recovery of the phosphoproteins and glycoproteins. Any method can be used to denature the proteins. The examples cited here are only for illustrative purposes.

TABLE 4

Method for the isolation of phosphorylated and glycosylated proteins by Lanthanum (III) precipitation.

| Step | Description | Amount, volume, etc. | Function | Comment |
|---|---|---|---|---|
| 1 | Provide phosphorylated protein and/or glycoprotein sample | 50 µL of sample | | Can be from cancer cells or human cerebrospinal fluid, etc. The sample may be whole protein or be digested to provide polypeptides or fragments of proteins. In some embodiments the sample pH may be adjusted before step 2 in order to reduce interaction of the metal ion with acetic groups on the proteins. |
| Optional 2 | Protein denaturation | Add 8 µL 10 mM DTT and 10 µL 45 mM nOGP to the sample | Ensures that all phospho-sites and glyco-sites are accessible | DTT: Dithiotreitol nOGP: 1-O-n-octyl-β-D-glucopyranoside |
| Optional 3 | Further denaturation | Incubate the sample for 5 min at 95° C. | Breaks up of disulfide bonds by DTT | |
| Optional 4 | Protein alkylation | Add 10 µL of 50 mM IAA and | Alkylation of the thiol-groups | IAA: Iodoacetamide. Alkylation ensures that |

TABLE 4-continued

Method for the isolation of phosphorylated and glycosylated proteins by Lanthanum (III) precipitation.

| Step | Description | Amount, volume, etc. | Function | Comment |
|---|---|---|---|---|
| | | incubate 30 min in the dark | | disulfides are not reformed. |
| 5 | Add Lanthanum (III), mix sample by vortex | 1.5 µL of 1M LaCl$_3$, | Forms insoluble salt complex with phosphorylated proteins Forms insoluble chelate complex with glycosylated proteins. | Cloudy solution is formed with some particulate falling to the bottom of vial. Other lanthanide metals will also form salt and complex insoluble precipitates. Lanthanum protein precipitate can be centrifuged at this point. |
| Optional 6 | Add KH$_2$PO$_4$, mix sample by vortex | 1.5 µL of 2M KH$_2$PO$_4$ | The phosphate anion forms La(PO$_4$) ppt with left over or unused metal cation (any La that did not bind to a protein). | In some embodiments the addition of phosphate ion can be performed before step 5. The precipitates of La-protein and La(PO$_4$) can be easily centrifuged at this point. |
| 7 | Centrifuge to form pellet | | | |
| Optional 8 | Re-suspend and wash the pellet once with urea and CHAPS in PBS buffer and then centrifuge again | 300 µL of 8M urea/ 1% CHAPS in PBS pH 7.4 | Denatures precipitated protein in pellet | Also, removes any non-specific adsorbed protein. Surfactant may also be added earlier with the addition of Lanthanum. |
| 9 | Re-suspend and wash the pellet 3 times with DI water, centrifuging after each wash | De-ionized water | Removes excess urea and surfactant and non specific adsorbed protein | |
| Optional 10 | Treat pellet with phosphate ion and optionally recover supernatant | 50 µL of 4M KH$_2$PO$_4$ and de-ionized water | Breaks up any La-glycosylate protein precipitate that was formed in Step 2. Phosphoproteins remain in pellet. Glycoproteins are in supernatant and are optionally recovered and analyzed by top down or bottom up analysis. | The pellet may be treated with centrifugation or another method. No extra co-ppt with phosphorylated proteins is formed because excess La metal cation has been removed. |
| Optional 11 | On pellet microwave-assisted trypsin digestion | Several steps | Releases fragments of proteins through digestion | Bottom up sample prep |
| Optional 12 (follows optional 11) | µLC-ESI-MS analysis or other method on supernatant | | | Bottom up analysis |
| Optional 13 | Re-dissolve pellet | 10 µL of 10% TFA | Releases the proteins | Top down sample prep |
| Optional 14 (follows optional 13) | CE, MALDI or other method analysis | | | Top down analysis |

Example 4

The Selectivity of La (III) for a Phosphoprotein from a Protein Mixture

The selectivity of La (III) was tested for the precipitation of a phosphoprotein out of a protein mixture. For this experiment, phosphoprotein α-casein (0.01 µg/ml) was added to a mixture of three non phosphoproteins: myoglobin (1 µg/ml), lysozyme (1 µg/ml) and bovine serum albumin (BSA) (1 µg/ml). Albumin is known to be a "sticky protein" prone to binding other proteins. Nonspecific protein-protein interactions, if present, would decrease the selectivity and reliability of the method by interacting and co-precipitating non-specific proteins together with the target phosphoproteins. To minimize these possible protein-protein interactions, 3-[(3-cholamidopropyl)dimethylammonio]-2-hydroxy-1-propanesulfonate (CHAPS) zwitterion detergent was added to the sample as described in Examples 2 and 3 (Tables 3 and 4).

Figure 1:
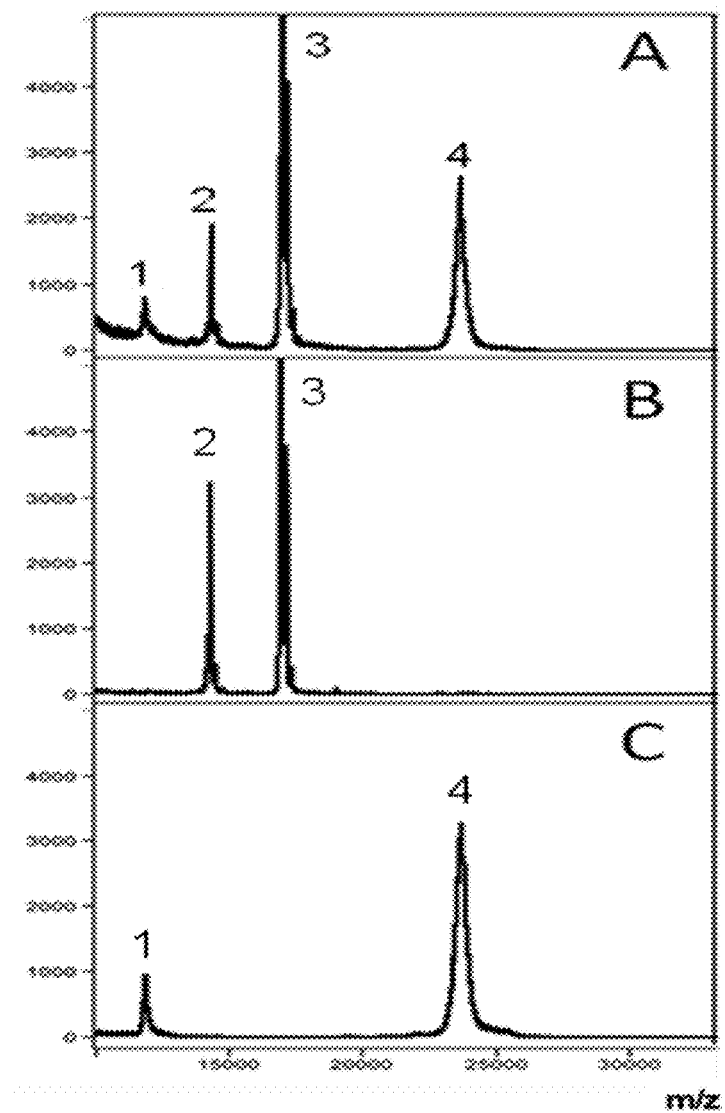
FIG. 1: MALDI-TOF spectra showing the isolation method for phosphoproteins.

The MALDI-TOF spectra (sinapinic acid matrix solution, 50% ACN, 0.1% TFA) results shown in FIG. 1 indicate the selectivity and efficiency of the precipitation method. Spectrum (A) shows the mixture before precipitation, (B) shows the spectrum of the supernatant after precipitation, and (C) shows the spectrum the precipitated pellet after it was denatured, washed and re-dissolved. Spectrum (B) shows that no signal was found for the phosphoprotein α-casein in the supernatant after the precipitation process, indicating the protein was completely precipitated as lanthanum-phosphoprotein complex. The spectrum shows that all the other non-phosphorylated proteins remained in the supernatant and MALDI-TOF peaks were still detected. Spectrum (C) showed that after dissolving the pellet, the α-casein phosphoprotein was recovered and detected with the same intensity.

Example 5

Isolation of Phosphoprotein in the Presence of Glycoproteins

The use of the reagent $KH_2PO_4$ was investigated to determine if it was possible to control the coprecipitation of glycoproteins with lanthanum cation while still precipitating phosphoproteins. In this scenario, the lanthanum would be added to the sample forming the phosphoprotein precipitate and the glycoprotein precipitate. Optionally, phosphate could be added at this point to form additional precipitate with any unused (unprecipitated or uncomplexed) metal ion. In alternate embodiments, the phosphate ions can be added before the lanthanide metal ion.

After washing the precipitate, phosphate anions can be added to the mixture to break up or redissolve the lanthanum glycoprotein precipitate while not disturbing the lanthanum phosphoprotein precipitate. This procedure may be used because only the stronger or more likely forming lanthanum phosphoprotein and lanthanum phosphate precipitate would be recovered while the lanthanum glycoprotein precipitate complexes would break up and redissolve. This provides a way to distinguish between phosphoproteins and certain glycoproteins. If excess phosphate ions are present in the sample, these phosphate ions might sequester the lanthanum and prevent or otherwise interfere with the desirable lanthanum phosphoprotein precipitation. It is surprising that the phosphate group contained on a protein forms a stable precipitate with lanthanum cation in the presence of phosphate anion. Furthermore, it is surprising that phosphate ions or other anions could facilitate the breaking up of a glycoprotein complex allowing the glycoprotein to re-dissolve when a lanthanum glycoprotein complex precipitate has already been formed. Precipitation reactions by nature may have very slow kinetic rate constants associated with the formation reaction and therefore precipitation and re-disolving may slow considerably or may appear to stop as the reagent concentrations are decreased. It is surprising and unexpected that lanthanide metal precipitation can be used to recover phosphoproteins and glycoproteins.

Figure 2:
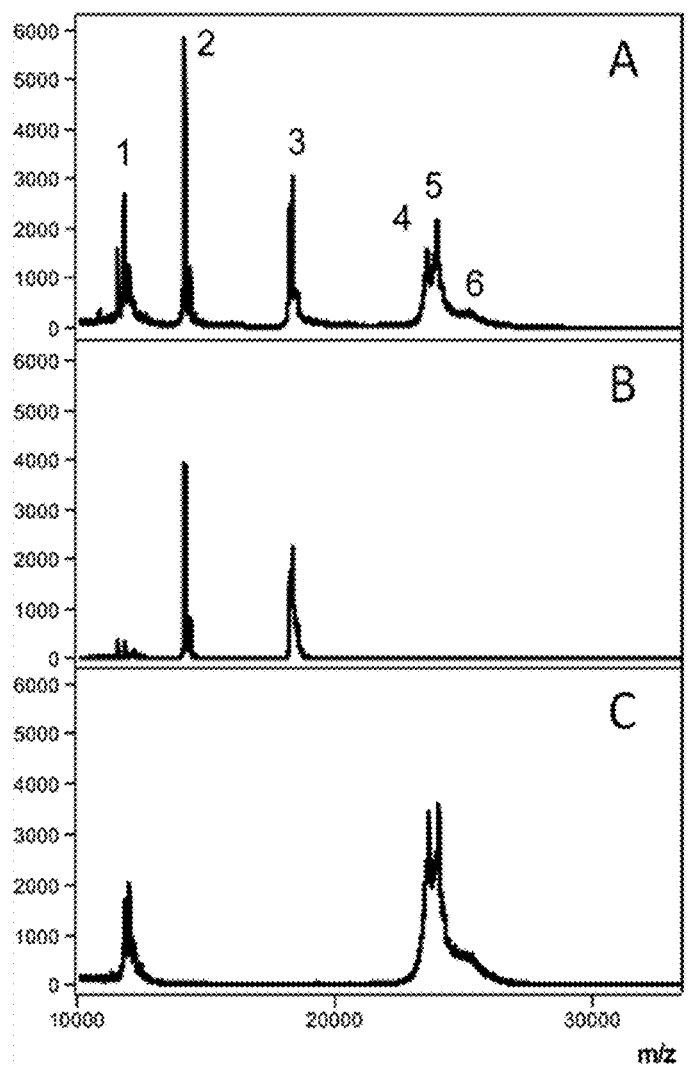
FIG. 2: MALDI-TOF spectra showing the isolation method for phosphoproteins in milk.

In order to study these selective precipitations and the related process of phosphoprotein isolation in the presence of glycoproteins, fresh milk was chosen as sample. This sample contained the phosphoproteins $\alpha s1$-casein, $\alpha s2$-casein and $\beta$-casein and the glycosylated protein $\alpha$-lactalbumin. The sample also contained the protein $\beta$-lactalbumin which does not contain either phosphorylated or glycosylated sites. The results are shown in FIG. 2. Spectrum (A) shows the MALDI-TOF spectrum of fresh milk before lanthanum precipitation (A). The labeled peaks are (1) $[M+2H]^{2+}$ caseins, (2) $[M+H]^+$ $\alpha$-lactalbumin, (3) $[M+H]^+$ $\beta$-lactoglobulin and (4) $[M+H]^+$ $\alpha S1$-casein, (5) $[M+H]^+$ $\beta$-casein and (6) $[M+H]^+$ $\alpha S2$-casein. The mass spectrum of the supernatant after lanthanum precipitation spectrum (B) show no caseins (phosphoproteins) can be detected in the supernatant. However, the mass of glycoprotein $\alpha$-lactalbumin was still detected with the same intensity showing the glycoprotein was not precipitated. The spectrum shows that $\beta$-lactoglobulin was also not precipitated. Spectrum (C) shows the recovered precipitated pellet shows the singly and doubly charged ion signal of caseins after denaturing, washing and re-dissolving the pellet.

On-Pellet Digestion

In a further step, the precipitated caseins were digested with trypsin directly on the pellet and measured by MALDI-TOF using DHB in 50% ACN, 0.1% TFA (puriss. p.a. Sigma-Aldrich, St. Louis, Mo., USA) as matrix. The mass peak list was submitted to the mascot search engine for peptide mass fingerprint (PMF) analysis and revealed 64% sequence coverage for $\alpha s1$-casein (15 masses identified), 51% for $\alpha s2$-casein (7 masses identified), and 20% for $\beta$-casein (6 masses identified). The recognized masses enabled a fast qualitative identification of the three casein proteins present in fresh milk due to the PMF.

The on-pellet digestion of precipitated lanthanum-protein complex was microwave-assisted. Several experiments were carried out for different energy levels and time periods. The best results were obtained for two minutes digestion at 70 W. At the same time, the un-precipitated protein mixture containing all four proteins was digested in-solution using the same protocol. The MALDI-TOF peak lists of both digests were submitted to the Mascot search engine for PMF analysis. No $\alpha$-casein could be significantly found in the digested un-precipitated protein mixture. This was probably due to suppression and interference effects from many other signals given off by proteins that are 100 times more highly concentrated in the sample. However, a Mascot search for the on-pellet digested lanthanum-protein complex yielded total sequence coverage of 92%.

Example 6

Isolation of $\alpha$-Casein from a Dephosphorylated HeLa Cell Lysate

Figure 3:
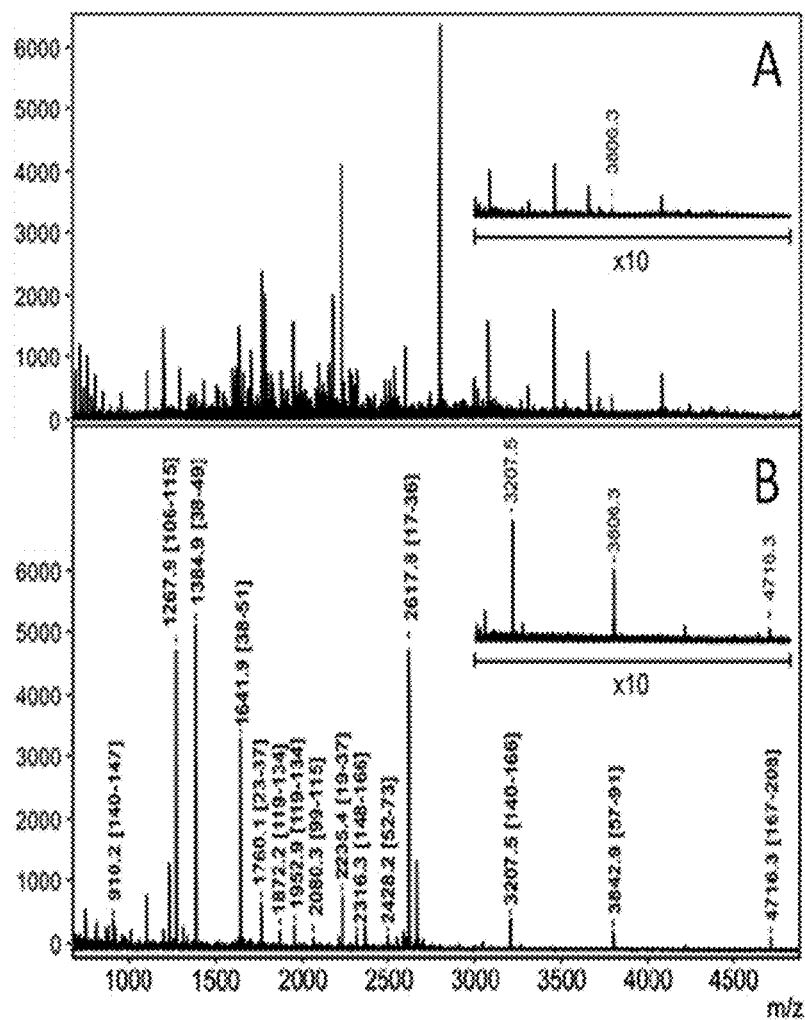
FIG. 3: MALDI-TOF spectra of tryptic digested HeLa cell lysate spiked with α-casein (1:100) before precipitation and after isolation.

A dephosphorylated HeLa cell lysate spiked with $\alpha$-casein (1:100) was analyzed with the developed strategy. FIG. 3 (top spectrum) depicts the MALDI-TOF (2,5-dihydroxybenzoic acid matrix) spectrum of a trypsin-digested HeLa cell lysate spiked with $\alpha$-casein that has not undergone the lanthanum precipitation sample process. The $\alpha$-casein could not be significantly detected in the un-precipitated digested protein mixture because of the huge amounts of peptides present in the sample. The same sample was treated with the lanthanum precipitation process and then treated with direct on-pellet digestion and measured by MALDI-TOF MS (bottom spectrum shown in FIG. 3). A Mascot search on the data by PMF analysis resulted in a sequence coverage of 87% for $\alpha$-casein (15 peptides identified with a score of 128). No other protein was present or could be identified.

Example 7

Analysis of Cerebrospinal Fluid Samples

In order to test the developed strategy with a complex biological sample of relevance to clinical proteomics, cerebrospinal fluid (CSF) samples were analyzed using the lanthanum precipitation procedure followed by on-pellet trypsin digestion and micro liquid chromatography electrospray ionization mass spectrometry (µLC-ESI-MS). The peptide identification was done by MS/MS. CSF is in contact with the whole central nervous system, surrounds the entire brain, and acts as an immunological and mechanical protection for the brain inside the skull. Thus, CSF reflects the biochemistry of the brain and changes in its protein composition and concentration are thought to be relevant for understanding chronic degenerative neurological diseases like Alzheimer's disease (AD), Creutzfeldt-Jakob disease, and multiple sclerosis. The determination of the concentration of beta amyloid 1-42 and tau protein in CSF, for example, is an important tool in the diagnosis of AD.

The analysis resulted in the identification of 53 phosphorylated and/or glycosylated proteins (Table 5). Twenty out of these have been mentioned in the literature as potential biomarkers for AD (Table 6). Previous published methods for the biomarker analysis including enzyme-linked immunosorbent assay (ELISA) applications, which take at least two hours (Wuhrer, M. et al. (2005) J. Chromatogr. A. 825, 124-133; Moon, Y. U. et al. (2000) J. Solution Chem. 29, 8) to perform while having lower performance due to non-specific binding problems (Scherz, H. et al. (1998) Analytical Chemistry of Carbohydrates, 1st Ed., pp. 275-276, Georg Thieme Verlag, Stuttgart.) In addition only a defined number of proteins can be bound in one analytical run in previous methods, while the precipitation method of the invention enables the simultaneous binding of phosphorylated and glycosylated proteins. Proteins which were recently described as phosphorylated like serum albumin, Dickkopf-related protein 3, SPARC-like protein 1 and apolipoprotein E36 (ApoE) were also successfully detected by this method in one single run.

TABLE 5

List of the identified proteins in CSF by µ-LC ESI MS/MS analysis after precipitation by Lanthanum (III).

| Accession number | Unique peptide detected | Sequence coverage % | Protein | Phosphorylation | Glycosylation |
|---|---|---|---|---|---|
| P02768 | 37 | 75.4 | Serum albumin | + | − |
| P02787 | 28 | 46.7 | Transferrin | + | + |
| P01024 | 20 | 19.9 | Human complement component C3 | + | + |
| O14594 | 2 | 3.1 | Neurocan core protein | − | + |
| P01009 | 9 | 31.1 | Alpha-1-antitrypsin | − | + |
| P06396 | 8 | 18.4 | Gelsolin | + | − |
| P00751 | 4 | 7.9 | Complement factor B | − | + |
| P02679 | 9 | 32.9 | Fibrinogen gamma chain | − | + |
| P00738 | 3 | 12.1 | Haptoglobin alpha chain | − | + |
| P0C0L4 | 11 | 13.0 | Acidic complement C4 | − | + |
| P05090 | 3 | 20.1 | Apolipoprotein D | − | + |
| P02751 | 8 | 5.5 | Fibronectin | + | + |
| P02675 | 3 | 7.5 | Fibrinogen beta chain | − | + |
| P10909 | 8 | 23.6 | Clusterin (ApoJ) | − | + |
| P00734 | 3 | 8.2 | Prothrombin | − | + |
| P05155 | 8 | 17.2 | Plasma protease C1 inhibitor | − | + |
| P01023 | 17 | 17.8 | Alpha-2-macroglobulin | − | + |
| P02652 | 4 | 41.0 | Apolipoprotein A - II | + | − |
| P05067 | 3 | 4.9 | Amyloid beta A4 protein | + | + |
| P02649 | 9 | 41.3 | Apolipoprotein E | + | + |
| P41222 | 4 | 36.3 | Prostaglandin - H2 D-isomerase | − | + |
| P01857 | 7 | 36.7 | Ig gamma-1 chain C region | − | + |
| P02766 | 5 | 68.7 | Transthyretin | − | + |
| P01042 | 4 | 8.5 | Kininogen-1 | + | + |
| Q14515 | 5 | 15.5 | SPARC-like protein 1 | + | + |
| P06727 | 2 | 5.5 | Apolipoprotein A - IV | + | − |
| P04004 | 4 | 10.9 | Vitronectin | + | + |
| P10451 | 5 | 27.7 | Osteopontin | + | + |
| P02760 | 2 | 6.5 | Alpha-1-microglobulin | − | + |
| Q8WXD2 | 4 | 12.2 | Secretogranin-3 | + | − |
| P01860 | 4 | 65.1 | Ig gamma-3 chain C region | − | + |
| P00450 | 6 | 9.4 | Ceruloplasmin | + | + |
| P13591 | 3 | 5.1 | Neural cell adhesion molecule 1 | + | + |
| Q9UBP4 | 7 | 33.1 | Dickkopf-related protein 3 | + | + |
| P02647 | 5 | 21.7 | Apolipoprotein A-I | + | + |
| P01011 | 4 | 15.8 | Alpha-1-antichymotrypsin | − | + |
| P01034 | 3 | 28.8 | Cystatin-C | + | − |
| P10645 | 4 | 16.0 | Chromogranin-A | + | + |
| P05060 | 8 | 17.6 | Secretogranin-1 | + | + |
| P01019 | 4 | 11.1 | Angiotensinogen | − | + |
| P36955 | 5 | 13.6 | Pigment epithelium-derived factor | + | + |
| O94985 | 3 | 4.5 | Calsyntenin-1 | − | + |
| Q06481 | 5 | 10.9 | Amyloid-like protein 1 | + | − |
| P23142 | 2 | 5.7 | Fibulin-1 | + | + |
| P20774 | 2 | 3.8 | Fibulin-3 | − | + |
| O00533 | 4 | 6.5 | Neuronal cell adhesion molecule L1-like protein | + | + |
| P02774 | 7 | 26.8 | Vitamin D-binding protein | − | + |
| P61769 | 2 | 18.5 | Beta-2-microglobulin | + | + |
| Q9UHG2 | 3 | 21.9 | Pro-SAAS | + | + |
| P02763 | 4 | 26.4 | Alpha-1-acid glycoprotein 1 | − | + |

TABLE 5-continued

List of the identified proteins in CSF by μ-LC ESI MS/MS analysis after precipitation by Lanthanum (III).

| Accession number | Unique peptide detected | Sequence coverage % | Protein | Phosphorylation | Glycosylation |
|---|---|---|---|---|---|
| Q99435 | 3 | 4.9 | Protein kinase C-binding protein NELL 2 | − | + |
| P02790 | 2 | 8.4 | Hemopexin | − | + |

TABLE 6

List of identified proteins in CSF samples analyzed by $La^{3+}$-precipitation that were found to be Alzheimer Disease (AD) related.

| Accession Number | Protein | Hit | Phosphorylation | Glycosylation |
|---|---|---|---|---|
| P05067 | Amyloid beta A4 protein | Ray, I. et al. (2000) Brain Research, 853, 344-351; Grimmer, T. et al. (2009) Biol. Psychiatry, 65, 927-934 | + | + |
| P06396 | Gelsolin | Ray, I. et al. (2000) Brain Research, 853, 344-351 | + | − |
| P01011 | Alpha-1-Anti-chymotrypsin | Eriksson, S. et al. (1995) Proc. Natl. Acad. Sci. USA, 92, 2313-2317; Gollin, P. et al. (1992) Neuro Report, 3, 127-210 | − | + |
| P02647 | Apolipoprotein A-I | Yin, G. N. et al. (2009) Brain Research, 1265, 158-170 | − | + |
| P02679 | Fibrinogen | Yin, G. N. et al. (2009) Brain Research, 1265, 158-170; Ojien van, M. et al. (2005) J. Am Hearth Assoc. 36, 2637-2641 | − | + |
| P00738 | Haptoglobin | Yin, G. N. et al. (2009) Brain Research, 1265, 158-170 | + | + |
| P02766 | Transthyretin | Biroccio, A. et al. (2006) Proteomics, 6, 2305-2313 | − | + |
| P10451 | Osteopontin | Wung, J. K. et al. (2007) Current Alzheimer Res. 4, 67-72 | − | + |
| Q14515 | SPARC-like protein 1 | Yin, G. N. et al. (2009) Brain Research, 1265, 158-170 | + | + |
| P02649 | Apolipoprotein E | Corder, E. H. et al. (1993) Science, 261, 921-923; Nguyen, T. T. et al. (2000) J. Clin Endocrinol. Metab. 85, 4354-4359 | + | + |
| P10909 | Clusterin | Yin, G. N. et al. (2009) Brain Research, 1265, 158-170. | − | + |
| Q9UBP4 | Dickkopf-related protein 3 | Zenzmaier, C. et al. (2004) J. of Neurochem. 110, 653-661 | + | + |
| P36955 | Pigment epithelium-derived factor | Yin, G. N. et al. (2009) Brain | + | + |

TABLE 6-continued

List of identified proteins in CSF samples analyzed by La³⁺-precipitation that were found to be Alzheimer Disease (AD) related.

| Accession Number | Protein | Hit | Phosphorylation | Glycosylation |
|---|---|---|---|---|
| | | Research, 1265, 158-170 | | |
| P02774 | Vitamin D-binding protein | Yin, G. N. et al. (2009) Brain Research, 1265, 158-170 | − | + |
| P01009 | Alpha-1-antitrypsin | Gollin, P. et al. (1992) Neuro Report, 3, 127-210 | − | + |
| P02763 | Alpha-1-acid glycoprotein 1 | Merritt, C. M. et al. (1988) Brain Res. Reviews, 66, 97-106 | − | + |
| P04004 | Vitronectin | Rogers, J. et al. (2000) Neurobiology of Aging, 21, 383-421 | + | + |
| P01042 | Kininogen-1 | Puchades, M. et al. (2003) Molecular Brain Res. 118, 140-146 | + | + |
| P01034 | Cystatin-C | Mi, W. et al. (2009) Nature Genetics, 39, 1440-1442 | + | − |
| P10645 | Chromogranin A | Lechner, T. et al. (2004) Experimental Gerontology, 39, 101-113 | + | + |

Example 8

Isolation of a Phosphoprotein and a Glycoprotein

As discussed above, it is possible to precipitate both phosphoproteins and glycoproteins and recover them in two different fractions. It was discovered that lanthanum (III) will bind and precipitate glycoproteins with lower affinity than phosphoproteins and phosphate ions. This property was used to perform the separation. The phosphoprotein α-casein and the glycoprotein lectin from fava beans were dissolved in deionized water (0.1 μg/ml). To 200 μL of the sample, 2 μL of 1M lanthanum chloride solution and optionally 1 μL of 2 M potassium hydrogen phosphate solution were added. After precipitate formation and centrifugation, a pellet was obtained. The pellet was resuspended in 500 μL water to wash and remove non precipitated proteins. This washing step was repeated two more times. In a first experiment the proteins were recovered at the same time by dissolving the pellet in 42.5% phosphoric acid in order to verify if the glycoprotein was still bound after the washing steps. The supernatant was spotted on a MALDI target with sinapinic acid as matrix. It was confirmed by MALDI-TOF that the glycoprotein was bound to the pellet.

The same experiment was repeated but after the washing steps the glycoprotein was eluted from the pellet by incubating the sample for 5 min at 800 rpm and 25° C. with 4 M potassium hydrogen phosphate solution. The supernatant with the eluted glycoprotein was collected and spotted on a MALDI target with sinapinic acid matrix confirming that the glycoprotein was released. It was confirmed that the precipitated phosphoprotein remained on the pellet. The pellet was dissolved in phosphoric acid, desalted and spotted on the MALDI target as described before. The phosphoprotein was detected but no glycoprotein was detected.

Figure 4:
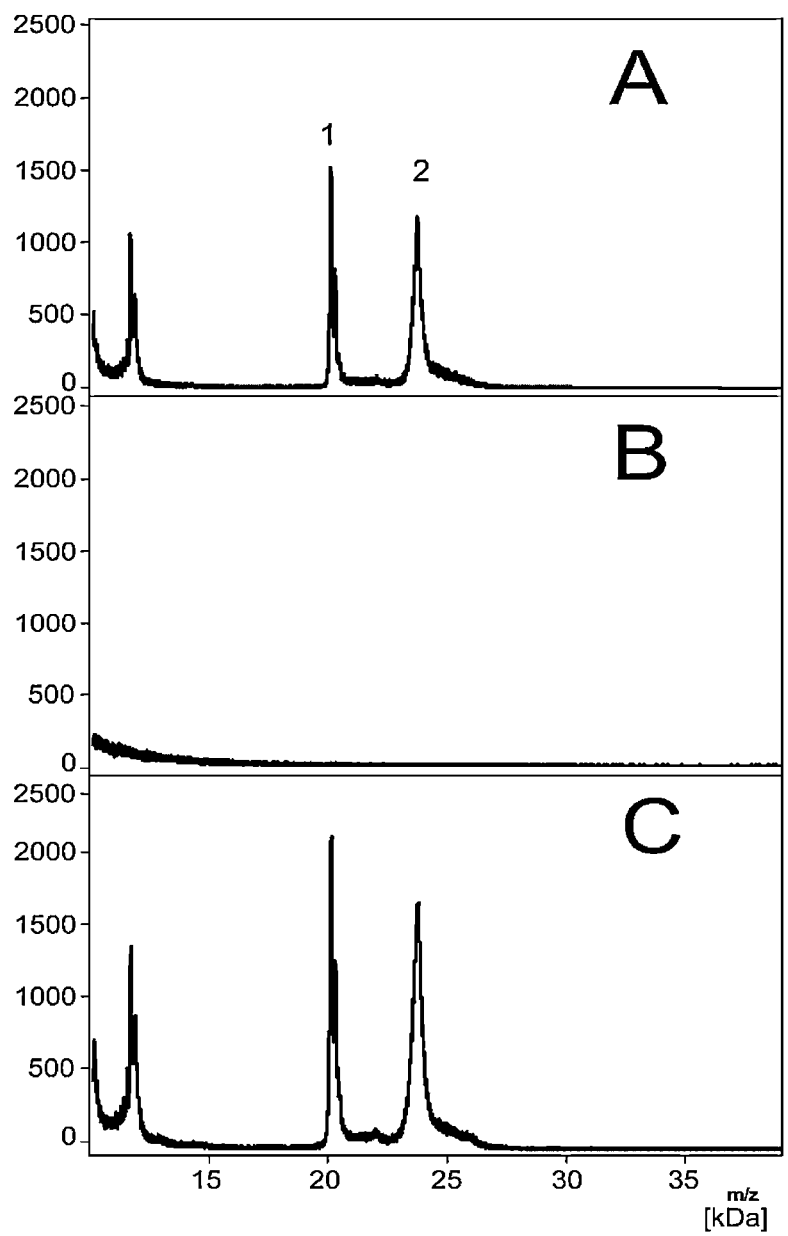
FIG. 4: MALDI-TOF spectra showing the precipitation and recovery of a phosphoprotein and glycoprotein.

The MALDI-TOF spectra in FIG. 4 shows that phosphoproteins and glycoproteins can be recovered together with no loss of glycoprotein. Glycoproteins can be precipitated simultaneously by trivalent La cations and recovered. Spectrum (A) shows both a glycoprotein (peak 1, lectin from fava beans) and a phosphoprotein (peak 2 beta casein) before the precipitation process. Spectrum (B) is the measurement of the supernatant demonstrating the successful precipitation of both proteins with no protein in the supernatant. Spectrum (C) shows both types of proteins were recovered and measured after the dissolving the pellet.

Example 9

Strategy for Selective Isolation of Phosphoproteins or Glycoproteins

Isolating phosphoproteins and/or glycoproteins in complex biological samples is challenging. The method depends on 1) discovering different selectivities of the two types proteins and 2) discovering some sort of separation procedure to take advantage of the selectivity differences. It was necessary to develop a targeted washing strategy for the selective isolation of phosphoproteins alone and glycoproteins alone. Among all the methods tried for removal of the glycosylated proteins from La³⁺ cations, a washing step of the precipitated pellet gave the best results. It was discovered that several types of wash solutions are effective. The wash solution could select for the glycoprotein. An example of this is boric acid or sodium borate solution. Alternatively, the wash solution could displace the glycoprotein. Examples of this are carbonate, oxalate, or hydroxide containing solutions. A solution of a $KH_2PO_4$ solution (e.g. 4 M) gave very good results and could be used to extract or elute the proteins from the metal precipitate pellet.

Figure 5:
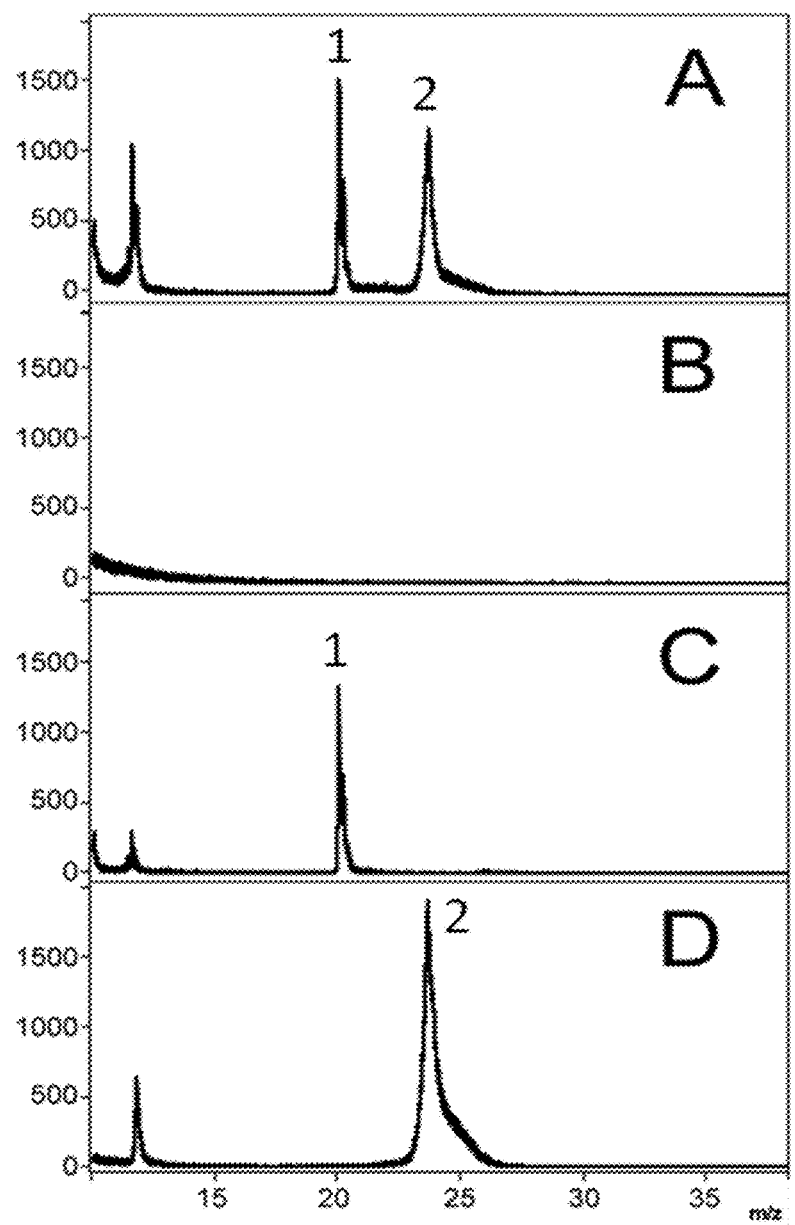
FIG. 5: MALDI-TOF spectra showing the precipitation, separation and recovery of a glycoprotein and a phosphoprotein.

FIG. 5 shows the MALDI-TOF spectra of the experiment performed with the $KH_2PO_4$ solution as the washing buffer. It is important that no glycoproteins are lost during the first washing steps, and that they are recovered later. The spectra show fractionation is achieved by adding concentrated phosphate to the pellet (for example 4M $KH_2PO_4$ solution), which will displace the precipitated La-glycoprotein complexes. Spectrum (A) shows the two standard glycoprotein lectin and phosphoprotein casein before precipitation and spectrum (B) the supernatant after precipitation in which no protein could be detected. To check the stability of the La-glycoprotein coordination complexes during the standard pellet washing steps, the supernatants from the three washing steps were pooled, desalted and measured by MALDI-TOF. Spectrum (C) shows the glycoprotein (lectin) recovered after the addition of a 4 M $KH_2PO_4$ solution. Spectrum (D) is the MALDI-TOF spectrum of the recovered phosphoprotein beta-casein after dissolving the pellet. No glycoprotein remained in the pellet.

The method fills an important need; the ability to isolate these proteins in a reproducible manner, especially when they are present at very low concentrations. Highly efficient, selective and reproducible capture is also necessary if the amount of protein present has to be quantified reliably. These results demonstrate that it is possible to simultaneously precipitate phosphoproteins and glycoproteins and then collect them in two different fractions for further analyses. It is also possible to precipitate phosphoproteins and glycoproteins at the same time and then separate the two fractions. Lanthanum will precipitate both types of proteins if the procedure is performed correctly. A lanthanide metal such as terbium, europium, or erbium can be chosen to selectivity precipitate phosphoproteins.

Table 7 shows the conditions for the application of the method to urine samples.

TABLE 7

Method that was used for the isolation of phosphorylated and glycosylated proteins by Lanthanum (III) precipitation from a urine sample. Urine samples usually require a larger volume to recover suitable proteins. Other parameters of the method can be varied as well. Comments and some of the possible variations on the method are included in the table.

| Step | Description | Amount, volume, etc. | Function | Comment |
|---|---|---|---|---|
| 1 | Urine sample was centrifuged first for 20 min to pellet the cells. | 1000 µL of sample | | Centrifuging down the cells contained in urine is the only pre-treatment needed. |
| 2 | Protein denaturation | Add 20 µl 10 mM DTT and 20 µl 45 mM nOGP to the sample | Ensured that all phospho-sites and glyco-sites are accessible to bind to the metal | DTT: Dithiotreitol nOGP: 1-O-n-octyl-β-D-glucopyranoside |
| 3 | Further denaturation | Incubated the sample for 5 min at 95° C. | Broke up the disulfide bonds by DTT | |
| 4 | Protein alkylation | Added 20 µl of 50 mM IAA and incubated 30 min in the dark | Alkylated the thiol-groups | IAA: Iodoacetamide Ensured that the disulphide bonds were not reformed. |
| 5 | Added Lanthanum (III), mixed sample by vortex | 5 µL of 1M $LaCl_3$ solution | Formed insoluble salt complex with phosphorylated proteins Formed insoluble chelate complex with glycosylated proteins. | Cloudy solution was formed with some particulate falling to the bottom of vial. |
| 6 | Added $KH_2PO_4$, mixed sample by vortex | 4 µL of 2M $KH_2PO_4$ solution | Formed additional ppt with unbound La cation. $La(PO_4)$ ppt increased the size of the pellet. | The pellet was more stable and easier to form. |
| 7 | Centrifuged | | | |
| 8 | Re-suspended and washed the pellet once with urea and CHAPS in PBS buffer and then centrifuged again | 500 µL of 8M urea/1% CHAPS in PBS pH 7.4 | Denatured precipitated proteins in pellet | Also, removed any non-specific adsorbed protein. Surfactant may also be added earlier with the addition of Lanthanum. |
| 9 | Re-suspended and washed the pellet 3 times with DI water, centrifuging after each wash | 500 µl de-ionized water | Removed excess urea and surfactant and non specific adsorbed proteins. The excess denaturing agents would otherwise affect the on-pellet tryptic digest. | |

TABLE 7-continued

Method that was used for the isolation of phosphorylated and glycosylated proteins by Lanthanum (III) precipitation from a urine sample. Urine samples usually require a larger volume to recover suitable proteins. Other parameters of the method can be varied as well. Comments and some of the possible variations on the method are included in the table.

| Step | Description | Amount, volume, etc. | Function | Comment |
|---|---|---|---|---|
| 10 | Treated pellet with phosphate ion and optionally keep supernatant | 50 µL of 4M $KH_2PO_4$ and de-ionized water | Broke up any La-glycoprotein precipitate that was formed in Step 2. No extra co-ppt with phosphorylated proteins is formed because excess La (III) has been removed. Phosphoproteins remain in pellet. Glycoproteins are in supernatant, can be further analyzed by top down or bottom up analysis. | The pellet may be centrifuged. |
| 11 | On pellet microwave-assisted trypsin digestion | Several steps | Released mostly non-phosphorylated peptides through digestion from the pellet | Bottom up sample preparation for protein identification by MS/MS analysis. |
| 12 | µLC-ESI-MS analysis or other method on supernatant | | | Bottom up analysis |
| Optional 13 | Re-dissolve pellet | 20 µL of 10% TFA | Releases the phosphoproteins | Top down sample preparation |
| Optional 14 (follows optional 13) | SDS-PAGE, MS or other instrumental analysis method | | | Top down analysis |

Example 10

Precipitation of Phospho-Proteins Using Lanthanum Chloride

A protein mixture consisting of α-casein (0.1 µg/µL), lysozyme (1 µg/µL), myoglobin (1 µg/µL), and BSA (1 µg/µL) (all purchased from Sigma-Aldrich, St. Louis, Mo., USA) was used as the standard sample. 1.5 µL of a lanthanum chloride solution (1 M) (puriss. p.a., Sigma-Aldrich, St. Louis, Mo., USA) was added to 50 µL of the sample followed by vortex-mixing. In a further step, 1.5 µL of a 2 M $KH_2PO_4$ (99.9%, Sigma-Aldrich, St. Louis, Mo., USA) solution were added. The resultant precipitate was centrifuged and washed by resuspending the pellet once in 500 µL of a mixture of 8 M urea solution and 1% CHAPS in PBS buffer (pH 7.4) (>98% Sigma-Aldrich, St. Louis, Mo., USA) and then washed three more times in 500 µL deionized water. In order to elute the bound proteins, the pellet was dissolved in 10 µL of 2.5% $H_3PO_4$ and analyzed by MALDI-TOF.

Example 11

On-Pellet Microwave-Assisted Tryptic Digest of Lanthanum Pellets

The pellet from Example 1 was used to perform an on-pellet microwave-assisted tryptic digest. The procedure provided a direct screening of the bound proteins on the pellet. After the washing steps and centrifugation, 16 µL of $NH_4HCO_3$ solution (0.5 M) (99.5%, Sigma-Aldrich, St. Louis, Mo., USA), 6 µL nOGP (45 mM) (98% Sigma-Aldrich St. Louis, Mo., USA), and 5 µL DTT (10 mM) (>99%, Sigma-Aldrich, St. Louis, Mo., USA) were added to the lanthanum phosphate pellet which was then incubated at 99° C. and 800 rpm for 5 minutes. After cooling to room temperature, 5 µL of IAA (50 mM) (crystalline, Sigma-Aldrich, St. Louis, Mo., USA) were added, and the sample was put in the dark for 30 minutes. In the next step, 70 µL of deionized water and 8 µL of trypsin (0.1 µg/µL) (sequencing grade modified, Promega, Mannheim, Germany) were added. The sample was then transferred to the microwave, and the digestion process was performed at 70 W for 2 minutes. The tryptic activity was stopped by the addition of 30 µL TFA (2%) (purum ≥99.5%, Fluka (Buchs, Switzerland). Finally, 1 µL of the sample was spotted on a MALDI stainless steel target (Bruker Daltonics GmbH, Bremen, Germany), followed by the addition of 1 µL of 2,5-dihydroxybenzoic acid.

Example 12

Analysis of CSF by Lanthanum (III) Precipitation

Twenty CSF samples were analyzed by lanthanum (III) precipitation. Excess CSF samples from the clinical routine at the Clinical Neurochemistry Laboratory at the Sahlgrenska University Hospital (Sweden) were included in the study. The CSF was obtained by lumbar puncture that was performed on clinical indication to exclude infections or inflammatory diseases of the central nervous system. The CSF was immediately transported to the laboratory, centrifuged at 1600×g for 10 min, aliquoted and stored at −80° C. pending analysis. Samples with greater than 500 erythrocytes/μL were excluded from the study. To 100 μL of each sample, 8 μL of a lanthanum chloride solution (1 M) were added. After a short vortex mixing, 8 μL of a potassium hydrogen phosphate solution (2 M) were added to increase the stability of the resulting pellet as well as to bind excess lanthanum (III). At this time, a smaller amount of the phosphate solution was added in order not to inhibit the lanthanum (III) glycoprotein interactions.

In another set of experiments 1 mL CSF was used and 6 μl of 1M lanthanum chloride and 5 μL 2M potassium hydrogen phosphate solution was used. The precipitate was then centrifuged and washed four times First with 500 μL of a mixture of 8 M urea solution and 1% CHAPS in PBS buffer (pH 7.4) and then with 500 μL deionized water. In order to digest the bound proteins, the same protocol as described before was used. The resulting peptides were then analyzed by μLC-ESI-MS and identified by Sequest against the SwissProt *Homo sapiens* database.

MALDI-TOF MS, μLC-ESI-MS and MS/MS analysis including database searching analysis was used for the sample analysis. For the sample preparation, 1 μL of the digest was spotted on a stainless steel target (Bruker Daltonics GmbH, Bremen, Germany) followed by adding 1 μL of a saturated dihydroxybenzoic acid matrix (50% ACN solution containing 1% $H_3PO_4$ and 0.1% TFA). For the measurement of the intact proteins, sinapinic acid (50% ACN solution containing 0.1% TFA) was applied as matrix. All the measurements were recorded by an Ultraflex I (Bruker Daltonics, Germany) MALDI-TOF/TOF MS in reflector and lift mode for MS/MS analysis. All mass spectra were recorded by summing 400 laser shots. The laser power was adjusted to between 30 and 50% of its maximal intensity, using a 337-nm nitrogen laser with a frequency of 50 Hz. The Flex Analysis version 2.4 and BioTools 3.0 software packages provided by the manufacturer were used for data processing. Peptide database searching analysis was performed with Mascot software (http://matrixscience.com) and Swiss Prot as database. For MS/MS search, the parameters were the following: C-carbamidomethyl (fixed modification), M-oxidation, ST-phosphorylation, γ-phosphorylation (variable modification), mass value (monoisotopic), peptide mass tolerance (120 ppm), mass tolerance (0.6 Da), missed cleavage (1), taxonomy ("mammalian" and for lysozyme "all entries") and a S/N threshold of 4.

For the μLC-ESI-MS analysis, tryptic digests were separated using micro high performance liquid chromatography and analyzed by electrospray Iontrap MS and MS/MS. The Agilent 1100 series system included a Nanoflow Pump with micro vacuum degasser, a Capillary Pump with micro vacuum degasser, a thermostated micro well-plate autosampler, a thermostated column compartment, and an external 2 position/10-port valve (Agilent Technologies, Santa Clara, Calif., USA). A 300 μm ID×5 mm 5 μm C18 100 Å PepMap trapping column and an Acclaim PepMap C18, 3 μm, 100 Å, 75 μm ID, and 50 cm separation column (Dionex, Amsterdam, The Netherlands) were used. After the loading of 7 μL onto the trapping column with a flow rate of 20 μL/min for 3 min, the separation was performed under reversed phase conditions with solvent A 2% acetonitrile (ACN) and 0.1% (v/v) formic acid (FA) in water and solvent B 0.1% (v/v) FA in 80% ACN, at a flow rate of 150 mL/min and 40° C. A linear gradient (50 min from 0% B to 60% B) was used. Hyphenation to the mass spectrometer was carried out by a nanoflow ESI source from Proxeon (Odense, Denmark) with Pico Tips from New Objective (FS360-20-10, MA, USA). Mass spectrometric data were obtained on the linear ion trap LTQ from Thermo Fisher (Thermo Fisher Scientific Inc., Waltham, Mass.). Measurements were performed as follows: source voltage −1.7 kV, capillary temperature 220° C., capillary voltage 22 V, and tube lens 129 V.

Data acquisition and interpretation was done with Xcalibur from Thermo Fisher (Thermo Fisher Scientific Inc., Waltham, Mass.). Database search was carried out with Bioworks Browser 3.3.1 SP1 (Thermo Fisher Scientific Inc., Waltham, Mass.) and Sequest against the SwissProt *Homo sapiens* database updated Apr. 22, 2010, 20166 sequences, carbamidomethylation on C as fixed modification, as well as oxidation of M and phosphorylation of S, T and Y as variable modifications and 3 possible missed cleavage sites. The following parameters were used to filter the identified proteins: for peptides a Sf—final score of 0.65, Xcorr vs. charge state for single, double and triple charged 1.50, 1.60, 2.00, 3.00 and a peptide probability of 1×10-4; for proteins a Sf—final score of 2.00 and a minimum number of 2 distinct peptides per protein. To obtain a high confidence for the identified proteins the peptides were checked manually and a reverse data base search was performed. The reverse data base search resulted in 0% false positive confirming the filter as used was reliable.

Example 13

Precipitation of Phosphorylated Proteins

A protein standard was prepared containing lysozyme, cytochrome c, myoglobin, bovine serum albumin, α- and β-casein at a concentration of 1 mg/mL, respectively. For protein denaturation, 100 μL of 40 mM nOGP and 100 μL of 45 mM DTT were added to a volume of 1 mL protein standard. The standard was sonicated for 1 min and centrifuged for 10 min at 13,500 rpm. The supernatant was placed into separate vials at 50 μL aliquots, which were then placed on a thermomixer for 30 min at 37° C. (600 rpm) before precipitation.

After protein denaturation, 2.5 μL of precipitant (either 2 M Eu(III)-, Tb(III)- or Er(III) chloride solution) are added to a 50 μL aliquot of protein standard. In a further step 2.5 of 0.5 M $KH_2PO_4$ μL are slowly added. The co-precipitated phosphoproteins (turbid solution) are separated by 3 min centrifugation at 13,500 rpm in order to receive a white pellet. Subsequently the supernatants are removed and analyzed by MALDI-TOF MS. For removing all unprecipitated proteins, two washing steps with 200 μL 80 mM europium(III)-, terbium(III)- or erbium(III)-chloride solution are applied (depending on the employed precipitant). After washing the pellet two times with 200 μL DHB solution (110 mM in 0.5% ACN/0.5% TFA), a last washing step with 200 μL of deionized $H_2O$ is carried out. Finally, the pellet is dissolved in 30 μL of 30% formic acid and analyzed by MALDI-TOF MS using sinapinic acid as matrix.

Figure 7:
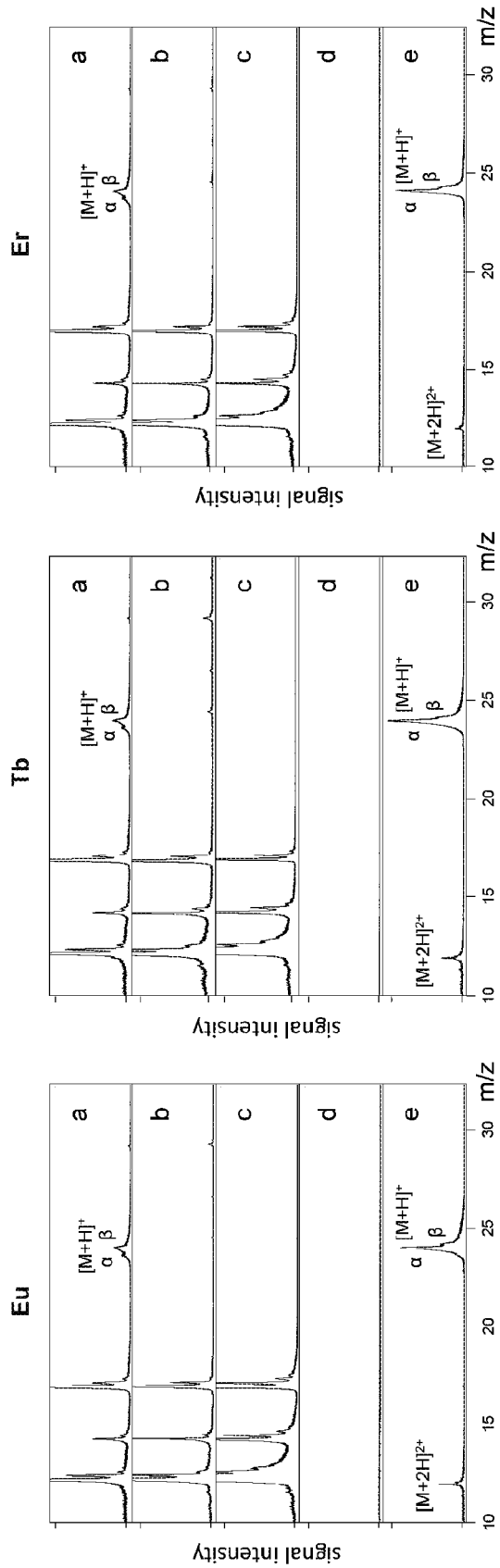
FIG. 7: MALDI-TOF spectra showing phosphoprotein precipitation from a protein standard by trivalent europium, terbium and erbium.

Mass spectra of the original protein standard are shown in section "a" of FIG. 7 for erbium(III), terbium(III) and europium(III) (BSA not recorded but present at m/z 69 kDa). Section "b" presents the supernatants after precipitation of phosphoproteins. No signals for α- and β-casein can be located in the mass spectra of the supernatants, indicating that they were completely precipitated. The recorded mass signals correlate with non-phosphorylated cytochrome c (m/z ~12.4 kDa), lysozyme (m/z ~14.4 kDa) and myoglobin (m/z ~16.2 kDa). Subsequent washing steps using a less concentrated solution of the corresponding precipitant were carried out to clean-up the pellet and to remove non-phosphorylated proteins (section "c" FIG. 7). An additional DHB washing step was found to be very effective in removing very small quantities of myoglobin (section "d" FIG. 7). For the DHB washing solution the amount of ACN was kept at a minimum of 0.5%, as increasing levels had been observed to partially dissolve the pellet. Excessive DHB was removed by washing with deionized water. The mass spectra of the dissolved protein-pellet demonstrate that only α-casein (m/z ~23.6 kDa) and β-casein (m/z ~24.0 kDa) are present in the pellet (FIG. 7e). This was also confirmed by further tryptic digestion of precipitated proteins including PMF analysis using the Mascot search engine. The best results could be achieved with europium, revealing 94% sequence coverage in case of α-casein and 67% for 3-casein. No other proteins could be significantly found by database searching analysis. The proteolytic activity of trypsin was found to be unaffected by the presence of lanthanide cations.

Example 14

Precipitation of Phosphorylated Peptides

Before phosphopeptide precipitation, 50 μL of enzymatic digest samples are adjusted to 100 μL with deionized water, respectively. Additionally, 3 μL of 0.5 M $KH_2PO_4$ and 3 μl_2 M lanthanide chloride solution ($LaCl_3$, $CeCl_3$, $EuCl_3$, $TbCl_3$, $HoCl_3$, $ErCl_3$ or $TmCl_3$) are added. The solutions are incubated on a thermomixer at 25° C. for 10 minutes, followed by five minutes of centrifugation at room temperature. Subsequently, the supernatants are removed and the pellet is extensively washed with the respective lanthanide chloride solution (80 mM). After centrifugation, the washing solution is removed. A second wash is performed with DHB solution (20 mg/mL DHB in 2% ACN/0.1% TFA), followed by a last washing step with 0.2% HCl solution. Finally, the resulting pellet is dissolved in 30 μL of 2% HCl and examined by MALDI-TOF MS using DHB (20 mg/50% ACN/0.1% TFA/ 1% phosphoric acid) as matrix.

What is claimed is:

1. A method for isolating phosphoproteins from a biological sample, comprising:
    a. providing a biological sample comprised of denatured phosphoproteins;
    b. providing a lanthanide metal cation;
    c. mixing the biological sample with the lanthanide metal cation, wherein at least a portion of the lanthanide metal cation forms a precipitate with the phosphoproteins in the biological sample; and
    d. recovering the precipitate.
2. The method of claim 1, wherein the metal cation is erbium.
3. The method of claim 1, wherein a co-precipitant is additionally mixed with the biological sample and the lanthanide metal cation in step (c).
4. The method of claim 3, wherein the co-precipitant is comprised of a phosphate anion.
5. The method of claim 4, wherein the co-precipitant is $KH_2PO_4$.
6. The method of claim 5, wherein the precipitate is recovered by centrifugation.
7. The method of claim 6, wherein the precipitate is washed at least once.
8. The method of claim 7, wherein following the wash, the precipitate is dissolved in a low pH solution.
9. The method of claim 8, wherein the lanthanide metal cation is erbium.
10. The method of claim 8, wherein the lanthanide metal cation is terbium.
11. A method of isolating phosphoproteins from a biological sample, comprising:
    a. providing a denatured biological sample, wherein the biological sample is comprised of phosphoproteins;
    b. providing a lanthanide metal cation, wherein the lanthanide metal cation is erbium, terbium or europium;
    c. providing a co-precipitant, wherein the co-precipitant is comprised of a phosphate anion;
    d. mixing the biological sample, lanthanide metal cation and the co-precipitant, wherein at least a portion of lanthanide metal cation forms a precipitate with the phosphoproteins in the biological sample and the co-precipitant; and
    e. recovering the precipitate by centrifugation.
12. The method of claim 11, wherein the co-precipitant is $KH_2PO_4$.
13. The method of claim 11, wherein following step (d), the precipitate is washed at least once.
14. The method of claim 13, wherein following the wash, the precipitate is dissolved in a low pH solution.
15. The method of claim 8, wherein the lanthanide metal cation is europium.

* * * * *